United States Patent [19]

Wei et al.

[11] Patent Number: 5,776,889
[45] Date of Patent: Jul. 7, 1998

[54] HYPERSENSITIVE RESPONSE INDUCED RESISTANCE IN PLANTS

[75] Inventors: Zhong-Min Wei; Steven V. Beer, both of Ithaca, N.Y.

[73] Assignee: Cornell Research Foundation, Inc., Ithaca, N.Y.

[21] Appl. No.: 891,254

[22] Filed: Jul. 10, 1997

Related U.S. Application Data

[63] Continuation of Ser. No. 475,775, Jun. 7, 1995, abandoned.

[51] Int. Cl.$^6$ .................... A01N 37/18; A01N 63/00; A01N 65/00; A61K 38/00
[52] U.S. Cl. .................... 514/2; 424/93; 435/500; 435/847
[58] Field of Search .................... 514/2; 424/93; 435/847, 800

[56] References Cited

U.S. PATENT DOCUMENTS

| | | | |
|---|---|---|---|
| 4,569,841 | 2/1986 | Liu | 424/93 |
| 4,597,972 | 7/1986 | Taylor | 426/36 |
| 4,601,842 | 7/1986 | Caple et al. | 252/70 |
| 4,740,593 | 4/1988 | Gonzalez et al. | 435/243 |
| 4,851,223 | 7/1989 | Sampson | 424/711 |
| 4,886,825 | 12/1989 | Ruess et al. | 514/383 |
| 4,931,581 | 6/1990 | Schurter et al. | 560/18 |
| 5,057,422 | 10/1991 | Bol et al. | 800/205 |
| 5,061,490 | 10/1991 | Paau et al. | 424/93 |
| 5,135,910 | 8/1992 | Blackburn et al. | 514/2 |
| 5,173,403 | 12/1992 | Tang | 435/6 |
| 5,217,950 | 6/1993 | Blackburn et al. | 514/2 |
| 5,243,038 | 9/1993 | Ferrari et al. | 536/23.1 |
| 5,244,658 | 9/1993 | Parke | 424/93 |
| 5,260,271 | 11/1993 | Blackburn et al. | 514/2 |
| 5,348,743 | 9/1994 | Ryals et al. | 424/94.61 |
| 5,494,684 | 2/1996 | Cohen | 424/523 |
| 5,523,311 | 6/1996 | Schurter et al. | 548/361 |
| 5,550,228 | 8/1996 | Godiard et al. | 536/24.1 |
| 5,552,527 | 9/1996 | Godiard et al. | 530/379 |

FOREIGN PATENT DOCUMENTS

| | | |
|---|---|---|
| WO 94/01546 | 1/1994 | WIPO. |
| WO 94/26782 | 11/1994 | WIPO. |
| WO 95/19443 | 7/1995 | WIPO. |

OTHER PUBLICATIONS

Boccara, et al., "Plant Defense Elicitor Protein Produced by *Erwinia chrysanthemi*," *Mechanisms of Plant Defense Responses*, p. 166 (1993).

Bauer, et al., "*Erwinia chrysanthemi hrp* Genes and Their Involvement in Soft Rot Pathogenesis and Elicitation of the Hypersensitive Response." *MPMI*, 7(5):573–81 (1994).

Stryer, "Enzymes are Highly Specific," *Biochemistry*, San Francisco: W.H. Freeman and Company, p. 116 (1975).

Keen et al., "Inhibition of the Hypersensitive Reaction of Soybean Leaves to Incompatible Pseudomonas spp. by Blasticidin S, or Elevated Temperature," *Physiological Plant Pathology*, 18:325–337 (1981).

Lerner "Tapping the Immunological Repertoire to Produce Antibodies of Predetermined Specificity," *Nature*, 299:592–596 (1982).

Staskawicz et al., "Cloned Avirulence Gene of *Pseudomonas Syringae* pv. *glycinea* Determines Race-specific Incompatibility on *Glycine max* (L.) Merr.," *Proc. Natl. Acad. Sci.*, 81:6024–6028 (1984).

Atkinson et al., "The Hypersensitive Reaction of Tobacco to *Pseudomonas Syringae* pv. *pisi*$^1$," *Plant Physiol.*, 79:843–847 (1985).

Huynh et al., "Bacterial Blight of Soybean: Regulation of a Pathogen Gene Determining Host Cultivar Specificity," *Science*, 245:1374–1377 (1986).

Lindgren et al., "Gene Cluster of *Pseudomonas Syringae* pv. *Phaseolicola J. Bacteriology*, Controls Pathogenicity of Bean Plants and Hypersensitivity on Nonhost Plant," 168(2):512–522 (1986).

Bauer et al., "Cloning of a Gene from *Erwinia Aylovora* Involved in Induction of Hypersensitivity and Pathogenicity," *Plant Pathogenic Bacteria*, 425–429 (1987).

Collinge et al., "Plant Gene Expression in Response to Pathogens," *Plant Molecular Biology*, 9:389–410 (1987).

Shatzman et al., "Expression, Identification, and Characterization of Recombinant Gene Products in *Escherichia coli*," *Methods in Enzymology*, 152:661–673 (1987).

Shields, "Towards Insect-Resistant Plants," *Nature*, 328:12–13 (1987).

Huang et al., "Molecular Cloning of a *Pseudomonas syringae* pv. syringae Gene Cluster That Enables *Pseudonmonas fluorescens* To Elicit the Hypersensitive Response in Tobacco Plants," *Journal of Bacteriology*, 170(19)4748–4756 (1988).

Schottens-Toma et al., "Purification and Primary Structure of a Necrosis-inducing Peptide from the Apoplastic Fluids of Tomato Infected with *Cladosporium fulvum* (syn. Fulvia fulva)," *Physiological and Molecular Plant Pathology*, 33:59–67 (1988).

Steinberger et al., "Creation and Complementation of Pathogenicity Mutants of *Erwinia Amylovora*," *Molecular Plant-Microbe Interactions*, 1(3):135–144 (1988).

Beer et al., "The Hypersensitive Response is Elicited by *Eschericia Coli* Containing a Cluster of Pathogenicity Genes from *Erwinia Amylovora*," *Phytopathology*, 79(10):1156 (Abstract 169) (1989).

Hiatt et al., "Production of Antibodies in Transgenic Plants," *Nature*, 342:76–78 (1989).

(List continued on next page.)

Primary Examiner—Robert J. Hill, Jr.
Assistant Examiner—Jennifer Harle
Attorney, Agent, or Firm—Nixon, Hargrave, Devans & Doyle LLP

[57] ABSTRACT

The present invention relates to a method of imparting pathogen resistance to plants. This involves applying a hypersensitive response elicitor polypeptide or protein in a non-infectious form to a plant under conditions where the polypeptide or protein contacts cells of the plant. The present invention is also directed to a pathogen resistant plant and a composition for imparting pathogen resistance to plants.

26 Claims, 2 Drawing Sheets

OTHER PUBLICATIONS

Hippe et al., "In Situ Localization of a Foreign Protein in Transgenic Plants by Immunoelectron Microscopy Following High Pressure Freeze Substitution and Low Temperature Embedding," *European Journal of Cell Biology*, 50:230–234(1989).

Huang et al., "Isolation and Purification of a Factor from *Pseudomonas Solanacearum* That Induces a Hypresensitive–like Response in Potato Cells," *Molecular Plant–Microbe Interactions*, 2(3):132–138 (1989).

James et al., "Genetic Transformation of Apple (*Malus pumia* Mill.) Using a Disarmed Ti–binary Vector," *Plant Cell Reports*, 7:658–661 (1989).

Laby et al., "Cloning and Preliminary Characterization of an HRP Gene Cluster *Erwinia Amylovora*," *Phytopathology*, 79(10):1211 (Abstract 607) (1989).

Dow et al., "Extracellular Proteases from *Xanthomonas campestris* pv. Campestris, the Black Rot Pathogen," *Applied and Environmental Microbiology*, 56(10):2994–2998 (1990).

Walters et al., "Gene for Pathogenicity and Ability to Cause the Hypersensitive Reaction Cloned from *Erwinia Amylovora*," *Physiological and Molecular Plant Pathology*, 36:509–521 (1990).

Wu et al., "Cloning, Genetic Organization, and Characterization of a Structural Gene Encoding Bacillopeptidase F from *Bacillus subtillis*," *The Journal of Biological Chemistry*, 265(12):6845–6850 (1990).

Bauer et al., "Further Characterization of an hrp Gene Cluster of *Erwinia Amylovora*," *Molecular Plant Microbe Interactions*,4(5):493–499 (1991).

Beer et al., "The HRP Gene Cluster of *Erwinia Amylovora*," *Advances in Molecular Genetics of Plant–Microbe Interactions*, 1:53–60 (1991).

Benvenuto et al., "Phytoantibodies': A General Vector for the Expression of Immunoglobulin Domains in Transgenic Plants," *Plant Molecular Biology*, 17:865–874 (1991).

Milat et al., "Physiological and Structural Changes in Tobacco Leaves Treated with Cryptogein, a Proteinaceous Elicitor from *Phytophthora cryptogea*," *Phytopathology*, 81(11):1364–1368 (1991).

Ruberti et al., "A Novel Class of Plant Proteins Containing a Homeodomain with a Closely Linked Leucine Zipper Motif," *The EMBO Journal*, 10(7):1787–1791 (1991).

Quigley et al., "Nucleotide Sequence and Expression of a Novel Glycine–Rich Protein from *Arabidopsis Thaliana*," *Plant Molecular Biology*, 17:949–952 (1991).

van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions*, 4(1)52–59 (1991).

Waldmann, "Monoclonal Antibodies in Diagnosis and Therapy," *Science*, 252:1657–1662 (1991).

Willis et al., "hrp Genes of Phytopathogenic Bacteria," *Molecular Plant–Microbe Interactions*, 4:(2) 132–138 (1991).

Beer et al., "Are Harpins Universal Elicitors of the Hypersensitive Response of Phytopathogenic Bacteria?," *Advances in Molecular Genetics of Plant–Microbe Interactions*, 2:281–286 (1992).

Laby et al., *Molecular Plant–Microbe Interactions*, 5(5):412 (1992).

Sandhu, *Crit. Rev. in Biotech.*, (92–review) 12:437–462, 1992.

Wei et al., "Harpin, Elicitor of the Hypersensitive Response Produced by the Plant Pathogen *Erwinia Amylovora*," *Science*, 257:85–88 (1992).

He et al., "*Pseudomonas syringae* pv. *syringae* Harpin$_{Pss}$: A Protein that is Secreted Via the Hrp Pathway and Elicits the Hypersensitive Response in Plants," *Cell*, 73:1255–1266 (1993).

Bonas, "Bacterial Home Goal by Harpins," *Trends in Microbiology*, 2:1–2 (1994).

Collmer et al., "*Erwinia chrysanthemi* and *Pseudomonas syringae*: Plant Pathogens Trafficking in Extracellular Virulence Proteins," 43–78 (1994).

Frederick et al., "The wts water–soaking genes of *Erwinia stewartii* are Related to hrp genes," Seventh International Symposium on Molecular Plant Microbe Interactions, Abstract No. 191 (Jun. 1994).

Wei et al., "Proteinaceous Elicitors of the Hypersensitive Response from *Xanthomonas campestris* pv. glycines," Seventh International Symposium on Molecular Plant Microbe Interactions, Abstract No. 244 (Jun. 1994).

Preston et al., "The HrpZ proteins of *Pseudomonas syringae* pvs. syringae, glycinea, and tomato are Encoded by an Operon Containing *Yersinia ysc* Honologs and Elicit the Hypersensitive Response in Tomato by not Soybean," *Mol. Plant–Microbe Interact.*, 8:717–732 (1995).

Bauer et al., "*Erwinia chrysanthemi* hrp Genes and their Involvement in Elicitation of the Hypersensitive Response," Sixth International Symposium on Molecular Plant Microbe Interactions, Abstract No. 146 (Jul. 1992).

Bauer et al., "*Erwinia chrysanthemi* Harpin$_{Ech}$: An Elicitor of the Hypersensitive Response that Contributes to Soft–Rot Pathogenes Pathogenesis," *MPMI*, 8(4):484 (1995).

Huang et al., "Characterization of the hrp Cluster from *Pseudomonas syringae* pv. syringae 61 and TnphoA Tagging of Genes Encoding Exported or Membrane–Spanning Hrp Proteins," *Molec. Plant–Microbe Interact.*, 4(5):469–476 (1991).

Huang et al. "The *Pseudomonas syringae* pv. syringae 61 hrpH Product, and Envelope Protein Required for Elicitation of the Hypersensitive Response in Plants," *J. of Bacteriology*, 174(21):6878–6885 (1992).

Bonas, "hrp Genes of Phytopathogenic Bacteria," *Current Topics in Microbio.*, 192:79–98 (1994).

Arlat et al., "PopA1, A Protein Which Induces a Hypersensitivity–Like Response in Specific Protein Genotypes is Secreted Via the Hrp Pathway of *Pseudomonas solanacearum*," *The EMBO J.*, 13(3):543–553 (1994).

Kessman et al., "Induction of Systemic Acquired Disease Resistance in Plants By Chemicals," *Ann. Rev. Phytopathol.*, 32:439–59 (1994).

Kelman, "The Relationship of Pathogenicity in *Pseudomonas Solanacearum* To Colony Appearance on a Tetrazolium Medium," *Phytopathology*, 44:693–695 (1954).

Winstead et al., "Inoculation Techniqes For Evaluating Resistance to *Pseudomonas Solanacearum*," *Phytopathology*, 42:628–634 (1952).

Ahl et al., "Iron Bound–Siderophores, Cyanic Acid, and Antibiotics Involved in Suppression of *Thielaviopsis basiocola* by a *Pseudomonas fluorescens* Strain," *J. Pathology*, 116:121–134 (1986).

Anderson et al., "Responses of Bean to Root Colonization with *Pseudomonas putida* in a Hydroponic System," *Phytopathology*, 75(9):992–995 (1985).

Gardner et al., "Growth Promotion and Inhibition by Antibiotic-Producing Fluorescent Pseudomonads on Citrus Roots," *Plant and Soil*, 77:103–113 (1984).

Kloepper, "Effect of Seed Piece Inoculation with Plant Growth–Promoting Rhizobacteria on Populations of *Erwinia carotovora* on Potato Roots and In Daughter Tubers," *Phytopathology*, 73:217–219 (1983).

Kloepper et al., "Plant Growth–Promoting Rhizobacteria on Canola (Rapseed)," *Plant Disease* 72:42–46 (1988).

Kloepper et al., "Enhanced Plant Growth by Siderophores Produced by Plant Growth–Promoting Rhizobacteria," *Nature*, 286:885–886 (1980).

Kloepper et al., "Pseudomonas Siderophores: A Mechanism Explaining Disease–Suppressive Soils," *Current Microbiology*, 4:317–320 (1980).

Kloepper et al., "Emergence–Promoting Rhizobacteria: Description and Implications for Agriculture," In: *Iron, Siderophores, and Plant Disease*, Swinborne (ed), Plenum, NY, 155–164 (1986).

Kloepper et al., "Relationships of in vitro Antibiosis of Plant Growth–Promoting Rhizobacteria to Plant Growth and the Displacement of Root Microflora," *Phytopathology*, 71:1020–1024 (1981).

Kloepper et al. "Effects of Rhizosphere Colonization by Plant Growth–Promoting Rhizobacteria on Potato Plant Development and Yield," *Phytopathology*, 70:1078–1082 (1980).

Kloepper et al., "Plant Growth Promotion Mediated by Bacterial Rhizosphere Colonizers,"In: *The Rhizosphere and Plant Growth*, Keister et al. (eds), 315–326 (1991).

Lifshitz et al., "Growth Promotion of Canola (rapseed) Seedlings by a Strain of *Pseudomonas putida* Under Gnotobiotic Conditions," *Microbiol*. 33:390–395 (1987).

Liu et al., "Induction of Systemic Resistance in Cucumber Against Bacterial Angular Leaf Spot by Plant Growth–Promoting Rhizobacteria," *Phytopathology*, 85:843–847 (1995).

Loper et al., "Influence of Bacterial Sources of Indole–3–acetic Acid Root Elongation of Sugar Beet," *Phytopathology*, 76:386–389 (1986).

Schroth et al., "Disease–Suppressive Soil and Root–Colonizing Bacteria," *Science*, 216:1376–1381 (1982).

Stutz et al., "Naturally Occurring Fluorescent Pseudomonads Involved in Suppression of Black Root Rot of Tobacco," *Phytopathology*, 76:181–185 (1986).

Wei et al., "Induction of Systemic Resistance of Cucumber to *Colletotrichum orbiculare* by Select of Plant Growth–Promoting Rhizobacteria," *Phytopathology*, 81:1508–1512 (1991).

Wei et al., "Induction of Systemic Resistance with Seed Treatment by PGPR Strains," pp. 191–194 (1995).

Weller, "Biological Control of Soilborne Plant Pathogens in the Rhizosphere with Bacteria," *Ann. Rev. Phytopathol.*, 26:379–407 (1988).

Young et al., "PGPR: Is There a Relationship Between Plant Growth Regulators and the Stimulation of Plant Growth or Biological Activity?," pp. 182–186 (1995).

Wei et al., "Induced Systemic Resistance by Select Plant Growth–Promoting Rhizobacteria Against Bacterial Wilt of Cucumber and the Beetle Vectors," *Phytopathology*, 86:1154, Abstract No. 313 (1995).

Wieringa–Brants et al., Induced Resistance in Hypersensitive Tobacco Mosaic Virus by Injection of Intercellular Fluid from Tobacco Plants with Systemic Acquired Resistance, *Phytopathology*, 118:165–170 (1987).

Malamy et al., "Salicylic Acid: A Likely Endogenous Signal in the Resistance Response of Tobacco to Viral Infection," *Science*, 250:1002–1004 (1990).

Dean et al., "Immunisation Against Disease: The Plant Fights Back," pp. 383–411 (1992).

Cameron et al., "Biologically Induced Systemic: Acquired Resistance in *Arabidopsis thaliana,*" *The Plant Journal*, 5(5):715–725 (1994).

Laby et al., "Structural and Functional Analysis of *Erwinia Amylovora* Harpin, An Elicitor of the Plant Hypersensitive Response," *Phytopathology*, 84:345 (1994).

Van Gijsegem et al., "Evolutionary Conservation of Pathogenicity Determinants Among Plant and Animal Pathogenic Bacteria," *Trends Microbiol.*, 1:175–180 (1993).

Kamoun, et al., "Extracellular Protein Elicitors from Phytophthora: Host–Specificity and Induction of Resistance to Bacterial and Fungal Phytopathogens," *Molecular Plant–Microbe Interactions*, 6(1):15–25 (1993).

Baillieul, et al., "A New Elicitor of the Hypersensitive Response in Tobacco: A Fungal Glycoprotein Elicits Cell Death, Expression of Defense Genes, Production of Salicylic acid, and induction of Systemic Acquired Resistance," *The Plant Journal*, 8(4):551–60 (1995).

Tenhaken, et al., "Function of the Oxidative Burst in Hypersensitive Disease Resistance," *Proc. Natl. Acad. Sci. USA*, 92:4158–63 (1995).

Bonnet, et al., "Acquired Resistance Triggered by Elicitins in Tobacco and Other Plants," *European Journal of Plant Pathology*, 102:181–92 (1996).

Bonnet, et al., "Induction de nécroses foliares, de protéines b et de résistance dans les interactions tabac Phytophthora," *Agronomie*, 6(9):829–37 (1986).

Gallitelli, et al., "Satellite–Mediated Protection of Tomato Against Cucumber Mosaic Virus: II. Field Test Under Natural Epidemic Conditions in Southern Italy," *Plant Disease*, 75(1):93–95 (1991).

Ahn, et al., "Effects of Chilling Periods on the Growth and Yield of Strawberry (*Fragaria grandifloro* EHRH) in Forcing Culture," 27(1):17–26 (1985).

Montasser, et al., "Satellite–Mediated Protection of Tomato Against Cucumber Mosaic Virus: I. Greenhouse Experiments and Stimulated Epidemic Conditions in the Field," *Plant Disease*, 75(1)86–92 (1991).

Marks, R.J., "Varietal Resistance to Potato Cyst Nematode," *Agricultural Entomology*, (1979).

Walton, et al., "Host–Selective Toxins and Disease Specificity: Perspectives and Progress," *Annu. Rev. Phytopathol.*, 31:275–303 (1993).

Atkinson, M.M., "Molecular Mechanisms of Pathogen Recognition by Plants," *Advances in Plant Pathology*, 10:36–64 (1993).

Godiard, et al., "Differential Regulation in Tobacco Cell Suspensions of Genes Involved in Plant–Bacteria Interactions by Pathogen–Related Signals," *Plant Molecular Biology*, 17:409–13 (1991).

Ricci, et al., "Structure and Activity of Proteins from Pathogenic Fungi Phytophthora Eliciting Necrosis and Acquired Resistance in Tobacco," *Eur. J. Biochem.*, 183:555–63 (1989).

Lakhmatova, I.T., "Induction of Plant Resistance to Viral Disease: Application of Vaccination," *Sel'skokhozyaistvennaya Biologiya*, 3:39–51 (1991).

*Biologicheskii Zhurnal Armenii*, 31(3):305–09 (1978).

Lakhmatova, L.T., "Using Biologically Active Substances to Induced Plant Resistance to Viruses Immunization," *Sel'skokhozyaistvennaya Biologiya*, 3:13–22 (1992).

Ricci, et al., "Differential Production of Parasiticein, and Elicitor of Necrosis and Resistance in Tobacco, by Isolates of *Phytophthora parasitica*," *Plant Pathology*, 41:298–307 (1992).

Honée, et al., "Molecular Characterization of the Interaction Between the Fungal Pathogen *Cladosporium Fulvum* and Tomato," *Advances in Molecular Genetics of Plant–Microbe Interactions*, 3:199–206 (1994).

Keller, et al., "Responses of Tobacco to Elicitins, Proteins Form Phytophthora Spp. Eliciting Acquired Resistance," *Advances in Molecular Genetics of Plant–Microbe Interactions*, 3:327–32 (1994).

Keen, et al., "Bacteria Expressing Avirulence Gene D Produce a Specific Elicitor of the Soybean Hypersensitive Reaction," *Molecular Plant–Microbe Interactions*, 3(2):112–21 (1990).

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 338 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:1:

```
Met Gln Ile Thr Ile Lys Ala His Ile Gly Gly Asp Leu Gly Val Ser
 1               5                  10                  15

Gly Leu Gly Ala Gln Gly Leu Lys Gly Leu Asn Ser Ala Ala Ser Ser
                20                  25                  30

Leu Gly Ser Ser Val Asp Lys Leu Ser Ser Thr Ile Asp Lys Leu Thr
            35                  40                  45

Ser Ala Leu Thr Ser Met Met Phe Gly Gly Ala Leu Ala Gln Gly Leu
        50              55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
                100                 105                 110

Leu Leu Gly His Asp Thr Val Thr Lys Leu Thr Asn Gln Ser Asn Gln
```

```
                                115                           120                            125
      Leu  Ala  Asn  Ser  Met   Leu  Asn  Ala  Ser  Gln  Met  Thr  Gln  Gly  Asn  Met
           130                       135                      140
      Asn  Ala  Phe  Gly  Ser   Gly  Val  Asn  Asn  Ala  Leu  Ser  Ser  Ile  Leu  Gly
      145                       150                      155                           160
      Asn  Gly  Leu  Gly  Gln   Ser  Met  Ser  Gly  Phe  Ser  Gln  Pro  Ser  Leu  Gly
                     165                       170                           175
      Ala  Gly  Gly  Leu  Gln   Gly  Leu  Ser  Gly  Ala  Gly  Ala  Phe  Asn  Gln  Leu
                     180                       185                      190
      Gly  Asn  Ala  Ile  Gly   Met  Gly  Val  Gly  Gln  Asn  Ala  Ala  Leu  Ser  Ala
                195                       200                       205
      Leu  Ser  Asn  Val  Ser   Thr  His  Val  Asp  Gly  Asn  Asn  Arg  His  Phe  Val
           210                       215                      220
      Asp  Lys  Glu  Asp  Arg   Gly  Met  Ala  Lys  Glu  Ile  Gly  Gln  Phe  Met  Asp
      225                       230                      235                           240
      Gln  Tyr  Pro  Glu  Ile   Phe  Gly  Lys  Pro  Glu  Tyr  Gln  Lys  Asp  Gly  Trp
                          245                      250                           255
      Ser  Ser  Pro  Lys  Thr   Asp  Asp  Lys  Ser  Trp  Ala  Lys  Ala  Leu  Ser  Lys
                     260                       265                      270
      Pro  Asp  Asp  Asp  Gly   Met  Thr  Gly  Ala  Ser  Met  Asp  Lys  Phe  Arg  Gln
                275                       280                      285
      Ala  Met  Gly  Met  Ile   Lys  Ser  Ala  Val  Ala  Gly  Asp  Thr  Gly  Asn  Thr
           290                       295                      300
      Asn  Leu  Asn  Leu  Arg   Gly  Ala  Gly  Gly  Ala  Ser  Leu  Gly  Ile  Asp  Ala
      305                       310                      315                           320
      Ala  Val  Val  Gly  Asp   Lys  Ile  Ala  Asn  Met  Ser  Leu  Gly  Lys  Leu  Ala
                          325                      330                           335
      Asn  Ala
```

( 2 ) INFORMATION FOR SEQ ID NO:2:

( i ) SEQUENCE CHARACTERISTICS:
        ( A ) LENGTH: 2141 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CGATTTTACC   CGGGTGAACG   TGCTATGACC   GACAGCATCA   CGGTATTCGA   CACCGTTACG      60
GCGTTTATGG   CCGCGATGAA   CCGGCATCAG   GCGGCGCGCT   GGTCGCCGCA   ATCCGGCGTC     120
GATCTGGTAT   TTCAGTTTGG   GGACACCGGG   CGTGAACTCA   TGATGCAGAT   TCAGCCGGGG     180
CAGCAATATC   CCGGCATGTT   GCGCACGCTG   CTCGCTCGTC   GTTATCAGCA   GGCGGCAGAG     240
TGCGATGGCT   GCCATCTGTG   CCTGAACGGC   AGCGATGTAT   TGATCCTCTG   GTGGCCGCTG     300
CCGTCGGATC   CCGGCAGTTA   TCCGCAGGTG   ATCGAACGTT   TGTTTGAACT   GGCGGGAATG     360
ACGTTGCCGT   CGCTATCCAT   AGCACCGACG   GCGCGTCCGC   AGACAGGGAA   CGGACGCGCC     420
CGATCATTAA   GATAAAGGCG   GCTTTTTTTA   TTGCAAAACG   GTAACGGTGA   GGAACCGTTT     480
CACCGTCGGC   GTCACTCAGT   AACAAGTATC   CATCATGATG   CCTACATCGG   GATCGGCGTG     540
GGCATCCGTT   GCAGATACTT   TTGCGAACAC   CTGACATGAA   TGAGGAAACG   AAATTATGCA     600
AATTACGATC   AAAGCGCACA   TCGGCGGTGA   TTTGGGCGTC   TCCGGTCTGG   GCTGGGTGC      660
TCAGGGACTG   AAAGGACTGA   ATTCCGCGGC   TTCATCGCTG   GGTTCCAGCG   TGGATAAACT     720
```

-continued

| | | | | | |
|---|---|---|---|---|---|
| GAGCAGCACC | ATCGATAAGT | TGACCTCCGC | GCTGACTTCG | ATGATGTTTG | GCGGCGCGCT | 780 |
| GGCGCAGGGG | CTGGGCGCCA | GCTCGAAGGG | GCTGGGGATG | AGCAATCAAC | TGGGCCAGTC | 840 |
| TTTCGGCAAT | GGCGCGCAGG | GTGCGAGCAA | CCTGCTATCC | GTACCGAAAT | CCGGCGGCGA | 900 |
| TGCGTTGTCA | AAAATGTTTG | ATAAAGCGCT | GGACGATCTG | CTGGGTCATG | ACACCGTGAC | 960 |
| CAAGCTGACT | AACCAGAGCA | ACCAACTGGC | TAATTCAATG | CTGAACGCCA | GCCAGATGAC | 1020 |
| CCAGGGTAAT | ATGAATGCGT | TCGGCAGCGG | TGTGAACAAC | GCACTGTCGT | CCATTCTCGG | 1080 |
| CAACGGTCTC | GGCCAGTCGA | TGAGTGGCTT | CTCTCAGCCT | TCTCTGGGGG | CAGGCGGCTT | 1140 |
| GCAGGGCCTG | AGCGGCGCGG | GTGCATTCAA | CCAGTTGGGT | AATGCCATCG | GCATGGGCGT | 1200 |
| GGGGCAGAAT | GCTGCGCTGA | GTGCGTTGAG | TAACGTCAGC | ACCCACGTAG | ACGGTAACAA | 1260 |
| CCGCCACTTT | GTAGATAAAG | AAGATCGCGG | CATGGCGAAA | GAGATCGGCC | AGTTTATGGA | 1320 |
| TCAGTATCCG | GAAATATTCG | GTAAACCGGA | ATACCAGAAA | GATGGCTGGA | GTTCGCCGAA | 1380 |
| GACGGACGAC | AAATCCTGGG | CTAAAGCGCT | GAGTAAACCG | GATGATGACG | GTATGACCGG | 1440 |
| CGCCAGCATG | GACAAATTCC | GTCAGGCGAT | GGGTATGATC | AAAAGCGCGG | TGGCGGGTGA | 1500 |
| TACCGGCAAT | ACCAACCTGA | ACCTGCGTGG | CGCGGGCGGT | GCATCGCTGG | GTATCGATGC | 1560 |
| GGCTGTCGTC | GGCGATAAAA | TAGCCAACAT | GTCGCTGGGT | AAGCTGGCCA | ACGCCTGATA | 1620 |
| ATCTGTGCTG | GCCTGATAAA | GCGGAAACGA | AAAAGAGAC | GGGGAAGCCT | GTCTCTTTTC | 1680 |
| TTATTATGCG | GTTTATGCGG | TTACCTGGAC | CGGTTAATCA | TCGTCATCGA | TCTGGTACAA | 1740 |
| ACGCACATTT | TCCCGTTCAT | TCGCGTCGTT | ACGCGCCACA | ATCGCGATGG | CATCTTCCTC | 1800 |
| GTCGCTCAGA | TTGCGCGGCT | GATGGGGAAC | GCCGGGTGGA | ATATAGAGAA | ACTCGCCGGC | 1860 |
| CAGATGGAGA | CACGTCTGCG | ATAAATCTGT | GCCGTAACGT | GTTTCTATCC | GCCCCTTTAG | 1920 |
| CAGATAGATT | GCGGTTTCGT | AATCAACATG | GTAATGCGGT | TCCGCCTGTG | CGCCGGCCGG | 1980 |
| GATCACCACA | ATATTCATAG | AAAGCTGTCT | TGCACCTACC | GTATCGCGGG | AGATACCGAC | 2040 |
| AAAATAGGGC | AGTTTTGCG | TGGTATCCGT | GGGGTGTTCC | GGCCTGACAA | TCTTGAGTTG | 2100 |
| GTTCGTCATC | ATCTTTCTCC | ATCTGGGCGA | CCTGATCGGT | T | | 2141 |

( 2 ) INFORMATION FOR SEQ ID NO:3:

( i ) SEQUENCE CHARACTERISTICS:
    ( A ) LENGTH: 385 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:3:

| Met | Ser | Leu | Asn | Thr | Ser | Gly | Leu | Gly | Ala | Ser | Thr | Met | Gln | Ile | Ser |
|---|---|---|---|---|---|---|---|---|---|---|---|---|---|---|---|
| 1 | | | | 5 | | | | | 10 | | | | | 15 | |

| Ile | Gly | Gly | Ala | Gly | Gly | Asn | Asn | Gly | Leu | Leu | Gly | Thr | Ser | Arg | Gln |
| | | | 20 | | | | | 25 | | | | | 30 | | |

| Asn | Ala | Gly | Leu | Gly | Gly | Asn | Ser | Ala | Leu | Gly | Leu | Gly | Gly | Gly | Asn |
| | | 35 | | | | | 40 | | | | | 45 | | | |

| Gln | Asn | Asp | Thr | Val | Asn | Gln | Leu | Ala | Gly | Leu | Leu | Thr | Gly | Met | Met |
| | 50 | | | | | 55 | | | | | 60 | | | | |

| Met | Met | Met | Ser | Met | Met | Gly | Gly | Gly | Gly | Leu | Met | Gly | Gly | Gly | Leu |
| 65 | | | | | 70 | | | | | 75 | | | | | 80 |

| Gly | Gly | Gly | Leu | Gly | Asn | Gly | Leu | Gly | Gly | Ser | Gly | Gly | Leu | Gly | Glu |
| | | | | 85 | | | | | 90 | | | | | 95 | |

| Gly | Leu | Ser | Asn | Ala | Leu | Asn | Asp | Met | Leu | Gly | Gly | Ser | Leu | Asn | Thr |

|     |     |     | 100 |     |     |     | 105 |     |     |     | 110 |     |     |     |
|-----|-----|-----|-----|-----|-----|-----|-----|-----|-----|-----|-----|-----|-----|-----|

Leu Gly Ser Lys Gly Gly Asn Asn Thr Thr Ser Thr Thr Asn Ser Pro
        115                   120                  125

Leu Asp Gln Ala Leu Gly Ile Asn Ser Thr Ser Gln Asn Asp Asp Ser
    130                  135                  140

Thr Ser Gly Thr Asp Ser Thr Ser Asp Ser Ser Asp Pro Met Gln Gln
145                  150                155                  160

Leu Leu Lys Met Phe Ser Glu Ile Met Gln Ser Leu Phe Gly Asp Gly
                165                170                175

Gln Asp Gly Thr Gln Gly Ser Ser Ser Gly Gly Lys Gln Pro Thr Glu
            180                  185                190

Gly Glu Gln Asn Ala Tyr Lys Lys Gly Val Thr Asp Ala Leu Ser Gly
        195                   200                 205

Leu Met Gly Asn Gly Leu Ser Gln Leu Leu Gly Asn Gly Gly Leu Gly
    210                  215                  220

Gly Gly Gln Gly Gly Asn Ala Gly Thr Gly Leu Asp Gly Ser Ser Leu
225                  230              235                  240

Gly Gly Lys Gly Leu Gln Asn Leu Ser Gly Pro Val Asp Tyr Gln Gln
            245                  250              255

Leu Gly Asn Ala Val Gly Thr Gly Ile Gly Met Lys Ala Gly Ile Gln
        260                  265                270

Ala Leu Asn Asp Ile Gly Thr His Arg His Ser Ser Thr Arg Ser Phe
    275                  280                285

Val Asn Lys Gly Asp Arg Ala Met Ala Lys Glu Ile Gly Gln Phe Met
    290                  295                300

Asp Gln Tyr Pro Glu Val Phe Gly Lys Pro Gln Tyr Gln Lys Gly Pro
305                  310              315                  320

Gly Gln Glu Val Lys Thr Asp Asp Lys Ser Trp Ala Lys Ala Leu Ser
            325                  330              335

Lys Pro Asp Asp Asp Gly Met Thr Pro Ala Ser Met Glu Gln Phe Asn
        340                  345              350

Lys Ala Lys Gly Met Ile Lys Arg Pro Met Ala Gly Asp Thr Gly Asn
    355                  360                365

Gly Asn Leu Gln His Ala Val Pro Val Val Leu Arg Trp Val Leu Met
    370                  375                380

Pro
385

( 2 ) INFORMATION FOR SEQ ID NO:4:

( i ) SEQUENCE CHARACTERISTICS:
        ( A ) LENGTH: 1158 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| ATGAGTCTGA | ATACAAGTGG | GCTGGGAGCG | TCAACGATGC | AAATTTCTAT | CGGCGGTGCG | 60 |
| GGCGGAAATA | ACGGGTTGCT | GGGTACCAGT | CGCCAGAATG | CTGGGTTGGG | TGGCAATTCT | 120 |
| GCACTGGGGC | TGGGCGGCGG | TAATCAAAAT | GATACCGTCA | ATCAGCTGGC | TGGCTTACTC | 180 |
| ACCGGCATGA | TGATGATGAT | GAGCATGATG | GGCGGTGGTG | GGCTGATGGG | CGGTGGCTTA | 240 |
| GGCGGTGGCT | TAGGTAATGG | CTTGGGTGGC | TCAGGTGGCC | TGGGCGAAGG | ACTGTCGAAC | 300 |
| GCGCTGAACG | ATATGTTAGG | CGGTTCGCTG | AACACGCTGG | GCTCGAAAGG | CGGCAACAAT | 360 |

| | | | | |
|---|---|---|---|---|
| ACCACTTCAA | CAACAAATTC | CCCGCTGGAC | CAGGCGCTGG | GTATTAACTC | AACGTCCCAA | 420 |
| AACGACGATT | CCACCTCCGG | CACAGATTCC | ACCTCAGACT | CCAGCGACCC | GATGCAGCAG | 480 |
| CTGCTGAAGA | TGTTCAGCGA | GATAATGCAA | AGCCTGTTTG | GTGATGGGCA | AGATGGCACC | 540 |
| CAGGGCAGTT | CCTCTGGGGG | CAAGCAGCCG | ACCGAAGGCG | AGCAGAACGC | CTATAAAAAA | 600 |
| GGAGTCACTG | ATGCGCTGTC | GGGCCTGATG | GGTAATGGTC | TGAGCCAGCT | CCTTGGCAAC | 660 |
| GGGGGACTGG | GAGGTGGTCA | GGGCGGTAAT | GCTGGCACGG | GTCTTGACGG | TTCGTCGCTG | 720 |
| GGCGGCAAAG | GGCTGCAAAA | CCTGAGCGGG | CCGGTGGACT | ACCAGCAGTT | AGGTAACGCC | 780 |
| GTGGGTACCG | GTATCGGTAT | GAAAGCGGGC | ATTCAGGCGC | TGAATGATAT | CGGTACGCAC | 840 |
| AGGCACAGTT | CAACCCGTTC | TTTCGTCAAT | AAAGGCGATC | GGGCGATGGC | GAAGGAAATC | 900 |
| GGTCAGTTCA | TGGACCAGTA | TCCTGAGGTG | TTTGGCAAGC | CGCAGTACCA | GAAAGGCCCG | 960 |
| GGTCAGGAGG | TGAAAACCGA | TGACAAATCA | TGGGCAAAAG | CACTGAGCAA | GCCAGATGAC | 1020 |
| GACGGAATGA | CACCAGCCAG | TATGGAGCAG | TTCAACAAAG | CCAAGGGCAT | GATCAAAAGG | 1080 |
| CCCATGGCGG | GTGATACCGG | CAACGGCAAC | CTGCAGCACG | CGGTGCCGGT | GGTTCTTCGC | 1140 |
| TGGGTATTGA | TGCCATGA | | | | | 1158 |

( 2 ) INFORMATION FOR SEQ ID NO:5:

( i ) SEQUENCE CHARACTERISTICS:
    ( A ) LENGTH: 341 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:5:

```
Met Gln Ser Leu Ser Leu Asn Ser Ser Leu Gln Thr Pro Ala Met
  1               5                  10                  15
Ala Leu Val Leu Val Arg Pro Glu Ala Glu Thr Thr Gly Ser Thr Ser
              20                  25                  30
Ser Lys Ala Leu Gln Glu Val Val Lys Leu Ala Glu Glu Leu Met
          35                  40                  45
Arg Asn Gly Gln Leu Asp Asp Ser Ser Pro Leu Gly Lys Leu Leu Ala
  50                  55                  60
Lys Ser Met Ala Ala Asp Gly Lys Ala Gly Gly Ile Glu Asp Val
 65                  70                  75                  80
Ile Ala Ala Leu Asp Lys Leu Ile His Glu Lys Leu Gly Asp Asn Phe
                  85                  90                  95
Gly Ala Ser Ala Asp Ser Ala Ser Gly Thr Gly Gln Gln Asp Leu Met
             100                 105                 110
Thr Gln Val Leu Asn Gly Leu Ala Lys Ser Met Leu Asp Asp Leu Leu
         115                 120                 125
Thr Lys Gln Asp Gly Gly Thr Ser Phe Ser Glu Asp Met Pro Met
     130                 135                 140
Leu Asn Lys Ile Ala Gln Phe Met Asp Asp Asn Pro Ala Gln Phe Pro
145                 150                 155                 160
Lys Pro Asp Ser Gly Ser Trp Val Asn Glu Leu Lys Glu Asp Asn Phe
                 165                 170                 175
Leu Asp Gly Asp Glu Thr Ala Ala Phe Arg Ser Ala Leu Asp Ile Ile
             180                 185                 190
Gly Gln Gln Leu Gly Asn Gln Ser Asp Ala Gly Ser Leu Ala Gly
         195                 200                 205
```

Thr Gly Gly Gly Leu Gly Thr Pro Ser Ser Phe Ser Asn Asn Ser Ser
        210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Gly Leu Gly Thr Pro Val
            260                 265                 270

Asn Thr Pro Gln Thr Gly Thr Ser Ala Asn Gly Gly Gln Ser Ala Gln
        275                 280                 285

Asp Leu Asp Gln Leu Leu Gly Gly Leu Leu Leu Lys Gly Leu Glu Ala
        290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
                325                 330                 335

Asn Gln Ala Ala Ala
                340

( 2 ) INFORMATION FOR SEQ ID NO:6:

( i ) SEQUENCE CHARACTERISTICS:
        ( A ) LENGTH: 1026 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | |
|---|---|---|---|---|---|
| ATGCAGAGTC | TCAGTCTTAA | CAGCAGCTCG | CTGCAAACCC | CGGCAATGGC | CCTTGTCCTG | 60 |
| GTACGTCCTG | AAGCCGAGAC | GACTGGCAGT | ACGTCGAGCA | AGGCGCTTCA | GGAAGTTGTC | 120 |
| GTGAAGCTGG | CCGAGGAACT | GATGCGCAAT | GGTCAACTCG | ACGACAGCTC | GCCATTGGGA | 180 |
| AAACTGTTGG | CCAAGTCGAT | GGCCGCAGAT | GGCAAGGCGG | GCGGCGGTAT | TGAGGATGTC | 240 |
| ATCGCTGCGC | TGGACAAGCT | GATCCATGAA | AAGCTCGGTG | ACAACTTCGG | CGCGTCTGCG | 300 |
| GACAGCGCCT | CGGGTACCGG | ACAGCAGGAC | CTGATGACTC | AGGTGCTCAA | TGGCCTGGCC | 360 |
| AAGTCGATGC | TCGATGATCT | TCTGACCAAG | CAGGATGGCG | GGACAAGCTT | CTCCGAAGAC | 420 |
| GATATGCCGA | TGCTGAACAA | GATCGCGCAG | TTCATGGATG | ACAATCCCGC | ACAGTTTCCC | 480 |
| AAGCCGGACT | CGGGCTCCTG | GGTGAACGAA | CTCAAGGAAG | ACAACTTCCT | TGATGGCGAC | 540 |
| GAAACGGCTG | CGTTCCGTTC | GGCACTCGAC | ATCATTGGCC | AGCAACTGGG | TAATCAGCAG | 600 |
| AGTGACGCTG | GCAGTCTGGC | AGGGACGGGT | GGAGGTCTGG | GCACTCCGAG | CAGTTTTTCC | 660 |
| AACAACTCGT | CCGTGATGGG | TGATCCGCTG | ATCGACGCCA | ATACCGGTCC | CGGTGACAGC | 720 |
| GGCAATACCC | GTGGTGAAGC | GGGGCAACTG | ATCGGCGAGC | TTATCGACCG | TGGCCTGCAA | 780 |
| TCGGTATTGG | CCGGTGGTGG | ACTGGGCACA | CCCGTAAACA | CCCCGCAGAC | CGGTACGTCG | 840 |
| GCGAATGGCG | GACAGTCCGC | TCAGGATCTT | GATCAGTTGC | TGGGCGGCTT | GCTGCTCAAG | 900 |
| GGCCTGGAGG | CAACGCTCAA | GGATGCCGGG | CAAACAGGCA | CCGACGTGCA | GTCGAGCGCT | 960 |
| GCGCAAATCG | CCACCTTGCT | GGTCAGTACG | CTGCTGCAAG | GCACCCGCAA | TCAGGCTGCA | 1020 |
| GCCTGA | | | | | | 1026 |

( 2 ) INFORMATION FOR SEQ ID NO:7:

(i) SEQUENCE CHARACTERISTICS:
  (A) LENGTH: 344 amino acids
  (B) TYPE: amino acid
  (C) STRANDEDNESS:
  (D) TOPOLOGY: linear (ii) MOLECULE TYPE: protein (xi) SEQUENCE DESCRIPTION: SEQ ID NO:7:

| Met | Ser | Val | Gly | Asn | Ile | Gln | Ser | Pro | Ser | Asn | Leu | Pro | Gly | Leu | Gln |
|---|---|---|---|---|---|---|---|---|---|---|---|---|---|---|---|
| 1 | | | | 5 | | | | | 10 | | | | | 15 | |
| Asn | Leu | Asn | Leu | Asn | Thr | Asn | Thr | Asn | Ser | Gln | Gln | Ser | Gly | Gln | Ser |
| | | | 20 | | | | 25 | | | | | 30 | | | |
| Val | Gln | Asp | Leu | Ile | Lys | Gln | Val | Glu | Lys | Asp | Ile | Leu | Asn | Ile | Ile |
| | | 35 | | | | | 40 | | | | | 45 | | | |
| Ala | Ala | Leu | Val | Gln | Lys | Ala | Ala | Gln | Ser | Ala | Gly | Gly | Asn | Thr | Gly |
| | 50 | | | | | 55 | | | | | 60 | | | | |
| Asn | Thr | Gly | Asn | Ala | Pro | Ala | Lys | Asp | Gly | Asn | Ala | Asn | Ala | Gly | Ala |
| 65 | | | | | 70 | | | | 75 | | | | | 80 | |
| Asn | Asp | Pro | Ser | Lys | Asn | Asp | Pro | Ser | Lys | Ser | Gln | Ala | Pro | Gln | Ser |
| | | | | 85 | | | | | 90 | | | | | 95 | |
| Ala | Asn | Lys | Thr | Gly | Asn | Val | Asp | Ala | Asn | Asn | Gln | Asp | Pro | Met |
| | | | 100 | | | | 105 | | | | | 110 | | |
| Gln | Ala | Leu | Met | Gln | Leu | Leu | Glu | Asp | Leu | Val | Lys | Leu | Leu | Lys | Ala |
| | | | 115 | | | | 120 | | | | | 125 | | | |
| Ala | Leu | His | Met | Gln | Gln | Pro | Gly | Gly | Asn | Asp | Lys | Gly | Asn | Gly | Val |
| | | 130 | | | | 135 | | | | | 140 | | | | |
| Gly | Gly | Ala | Asn | Gly | Ala | Lys | Gly | Ala | Gly | Gly | Gln | Gly | Gly | Leu | Ala |
| 145 | | | | | 150 | | | | | 155 | | | | | 160 |
| Glu | Ala | Leu | Gln | Glu | Ile | Glu | Gln | Ile | Leu | Ala | Gln | Leu | Gly | Gly | Gly |
| | | | | 165 | | | | | 170 | | | | | 175 | |
| Gly | Ala | Gly | Ala | Gly | Gly | Ala | Gly | Gly | Gly | Val | Gly | Gly | Ala | Gly | Gly |
| | | | 180 | | | | | 185 | | | | | 190 | | |
| Ala | Asp | Gly | Gly | Ser | Gly | Ala | Gly | Gly | Ala | Gly | Gly | Ala | Asn | Gly | Ala |
| | | 195 | | | | | 200 | | | | | 205 | | | |
| Asp | Gly | Gly | Asn | Gly | Val | Asn | Gly | Asn | Gln | Ala | Asn | Gly | Pro | Gln | Asn |
| | 210 | | | | | 215 | | | | | 220 | | | | |
| Ala | Gly | Asp | Val | Asn | Gly | Ala | Asn | Gly | Ala | Asp | Asp | Gly | Ser | Glu | Asp |
| 225 | | | | | 230 | | | | | 235 | | | | | 240 |
| Gln | Gly | Gly | Leu | Thr | Gly | Val | Leu | Gln | Lys | Leu | Met | Lys | Ile | Leu | Asn |
| | | | | 245 | | | | | 250 | | | | | 255 | |
| Ala | Leu | Val | Gln | Met | Met | Gln | Gln | Gly | Gly | Leu | Gly | Gly | Gly | Asn | Gln |
| | | | | 260 | | | | | 265 | | | | | 270 | |
| Ala | Gln | Gly | Gly | Ser | Lys | Gly | Ala | Gly | Asn | Ala | Ser | Pro | Ala | Ser | Gly |
| | | | 275 | | | | | 280 | | | | | 285 | | |
| Ala | Asn | Pro | Gly | Ala | Asn | Gln | Pro | Gly | Ser | Ala | Asp | Asp | Gln | Ser | Ser |
| | | 290 | | | | | 295 | | | | | 300 | | | |
| Gly | Gln | Asn | Asn | Leu | Gln | Ser | Gln | Ile | Met | Asp | Val | Val | Lys | Glu | Val |
| 305 | | | | | 310 | | | | | 315 | | | | | 320 |
| Val | Gln | Ile | Leu | Gln | Gln | Met | Leu | Ala | Ala | Gln | Asn | Gly | Gly | Ser | Gln |
| | | | | 325 | | | | | 330 | | | | | 335 | |
| Gln | Ser | Thr | Ser | Thr | Gln | Pro | Met | | | | | | | | |
| | | | 340 | | | | | | | | | | | | |

(2) INFORMATION FOR SEQ ID NO:8:

(i) SEQUENCE CHARACTERISTICS:

-continued (A) LENGTH: 1035 base pairs
(B) TYPE: nucleic acid
(C) STRANDEDNESS: single
(D) TOPOLOGY: linear ( i i ) MOLECULE TYPE: DNA (genomic)

( x i ) SEQUENCE DESCRIPTION: SEQ ID NO:8:

| | | | | | | |
|---|---|---|---|---|---|---|
| ATGTCAGTCG | GAAACATCCA | GAGCCCGTCG | AACCTCCCGG | GTCTGCAGAA | CCTGAACCTC | 60 |
| AACACCAACA | CCAACAGCCA | GCAATCGGGC | CAGTCCGTGC | AAGACCTGAT | CAAGCAGGTC | 120 |
| GAGAAGGACA | TCCTCAACAT | CATCGCAGCC | CTCGTGCAGA | AGGCCGCACA | GTCGGCGGGC | 180 |
| GGCAACACCG | GTAACACCGG | CAACGCGCCG | GCGAAGGACG | GCAATGCCAA | CGCGGGCGCC | 240 |
| AACGACCCGA | GCAAGAACGA | CCCGAGCAAG | AGCCAGGCTC | CGCAGTCGGC | CAACAAGACC | 300 |
| GGCAACGTCG | ACGACGCCAA | CAACCAGGAT | CCGATGCAAG | CGCTGATGCA | GCTGCTGGAA | 360 |
| GACCTGGTGA | AGCTGCTGAA | GGCGGCCCTG | CACATGCAGC | AGCCCGGCGG | CAATGACAAG | 420 |
| GGCAACGGCG | TGGGCGGTGC | CAACGGCGCC | AAGGGTGCCG | GCGGCCAGGG | CGGCCTGGCC | 480 |
| GAAGCGCTGC | AGGAGATCGA | GCAGATCCTC | GCCCAGCTCG | GCGGCGGCGG | TGCTGGCGCC | 540 |
| GGCGGCGCGG | GTGGCGGTGT | CGGCGGTGCT | GGTGGCGCGG | ATGGCGGCTC | CGGTGCGGGT | 600 |
| GGCGCAGGCG | GTGCGAACGG | CGCCGACGGC | GGCAATGGCG | TGAACGGCAA | CCAGGCGAAC | 660 |
| GGCCCGCAGA | ACGCAGGCGA | TGTCAACGGT | GCCAACGGCG | CGGATGACGG | CAGCGAAGAC | 720 |
| CAGGGCGGCC | TCACCGGCGT | GCTGCAAAAG | CTGATGAAGA | TCCTGAACGC | GCTGGTGCAG | 780 |
| ATGATGCAGC | AAGGCGGCCT | CGGCGGCGGC | AACCAGGCGC | AGGGCGGCTC | GAAGGGTGCC | 840 |
| GGCAACGCCT | CGCCGGCTTC | CGGCGCGAAC | CCGGGCGCGA | ACCAGCCCGG | TTCGGCGGAT | 900 |
| GATCAATCGT | CCGGCCAGAA | CAATCTGCAA | TCCCAGATCA | TGGATGTGGT | GAAGGAGGTC | 960 |
| GTCCAGATCC | TGCAGCAGAT | GCTGGCGGCG | CAGAACGGCG | GCAGCCAGCA | GTCCACCTCG | 1020 |
| ACGCAGCCGA | TGTAA | | | | | 1035 |

( 2 ) INFORMATION FOR SEQ ID NO:9:

( i ) SEQUENCE CHARACTERISTICS:
(A) LENGTH: 26 amino acids
(B) TYPE: amino acid
(C) STRANDEDNESS:
(D) TOPOLOGY: linear ( i i ) MOLECULE TYPE: peptide ( x i ) SEQUENCE DESCRIPTION: SEQ ID NO:9:

Thr Leu Ile Glu Leu Met Ile Val Val Ala Ile Ile Ala Ile Leu Ala
1               5                   10                  15

Ala Ile Ala Leu Pro Ala Tyr Gln Asp Tyr
            20                  25

HYPERSENSITIVE RESPONSE INDUCED RESISTANCE IN PLANTS

This application is a continuation of application Ser. No. 08/475,775, filed Jun. 7, 1995, now abandoned.

This invention was made with support from the U.S. Government under USDA NRI Competitive Research Grant No. 91-37303-6430.

FIELD OF THE INVENTION

The present invention relates to imparting hypersensitive response induced resistance to plants.

BACKGROUND OF THE INVENTION

Living organisms have evolved a complex array of biochemical pathways that enable them to recognize and respond to signals from the environment. These pathways include receptor organs, hormones, second messengers, and enzymatic modifications. At present, little is known about the signal transduction pathways that are activated during a plant's response to attack by a pathogen, although this knowledge is central to an understanding of disease susceptibility and resistance. A common form of plant resistance is the restriction of pathogen proliferation to a small zone surrounding the site of infection. In many cases, this restriction is accompanied by localized death (i.e., necrosis) of host tissues. Together, pathogen restriction and local tissue necrosis characterize the hypersensitive response. In addition to local defense responses, many plants respond to infection by activating defenses in uninfected parts of the plant. As a result, the entire plant is more resistant to a secondary infection. This systemic acquired resistance can persist for several weeks or more (R. E. F. Matthews, *Plant Virology* (Academic Press, New York, ed. 2, 1981)) and often confers cross-resistance to unrelated pathogens (J. Kuc, in *Innovative Approaches to Plant Disease Control*, I. Chet, Ed. (Wiley, New York, 1987), pp. 255–274, which is hereby incorporated by reference).

Expression of systemic acquired resistance is associated with the failure of normally virulent pathogens to ingress the immunized tissue (Kuc, J., "Induced Immunity to Plant Disease," *Bioscience*, 32:854–856 (1982), which is hereby incorporated by reference). Establishment of systemic acquired resistance is correlated with systemic increases in cell wall hydroxyproline levels and peroxidase activity (Smith, J. A., et al., "Comparative Study of Acidic Peroxidases Associated with Induced Resistance in Cucumber, Muskmelon and Watermelon," *Physiol. Mol. Plant Pathol.* 14:329–338 (1988), which is hereby incorporated by reference) and with the expression of a set of nine families of so-called systemic acquired resistance gene (Ward, E. R., et al., "Coordinate Gene Activity in Response to Agents that Induce Systemic Acquired Resistance," *Plant Cell* 3:49–59 (1991), which is hereby incorporated by reference). Five of these defense gene families encode pathogenesis-related proteins whose physiological functions have not been established. However, some of these proteins have antifungal activity in vitro (Bol, J. F., et al., "Plant Pathogenesis-Related Proteins Induced by Virus Infection," *Ann. Rev. Phytopathol.* 28:113–38 (1990), which is hereby incorporated by reference) and the constitutive expression of a bean chitinase gene in transgenic tobacco protects against infection by the fungus *Rhizoctonia solani* (Broglie, K., et al., "Transgenic Plants with Enhanced Resistance to the Fungal Pathogen Rhizoctonia Solani," *Science* 254:1194–1197 (1991), which is hereby incorporated by reference), suggesting that these systemic acquired resistance proteins may contribute to the immunized state (Uknes, S., et al., "Acquired Resistance in Arabidopsis," *Plant Cell* 4:645–656 (1992), which is hereby incorporated by reference).

Salicylic acid appears to play a signal function in the induction of systemic acquired resistance since endogenous levels increase after immunization (Malamy, J., et al., "Salicylic Acid: A Likely Endogenous Signal in the Resistance Response of Tobacco to Viral Infection," *Science* 250:1002–1004 (1990), which is hereby incorporated by reference) and exogenous salicylate induces systemic acquired resistance genes (Yalpani, N., et al., "Salicylic Acid is a Systemic Signal and an Inducer of Pathogenesis-Related Proteins in Virus-Infected Tobacco," *Plant Cell* 3:809–818 (1991), which is hereby incorporated by reference), and acquired resistance (Uknes, S., et al., "Acquired Resistance in Arabidopsis," *Plant Cell* 4:645–656 (1992), which is hereby incorporated by reference). Moreover, transgenic tobacco plants in which salicylate is destroyed by the action of a bacterial transgene encoding salicylate hydroxylase do not exhibit systemic acquired resistance (Gaffney, T., et al., "Requirement of Salicylic Acid for the Induction of Systemic Acquired Resistance," *Science* 261:754–296 (1993), which is hereby incorporated by reference). However, this effect may reflect inhibition of a local rather than a systemic signal function, and detailed kinetic analysis of signal transmission in cucumber suggests that salicylate may not be essential for long-distance signaling (Rasmussen, J. B., et al., "Systemic Induction of Salicylic Acid Accumulation in Cucumber after Inoculation with *Pseudomonas Syringae* pv. Syringae," *Plant Physiol.* 97:1342–1347) (1991), which is hereby incorporated by reference).

Immunization using biotic agents has been extensively studied. Green beans were systemically immunized against disease caused by cultivar-pathogenic races of *Colletotrichum lindemuthianum* by prior infection with either cultivar-nonpathogenic races (Rahe, J. E., "Induced Resistance in Phaseolus Vulgaris to Bean Anthracnose," *Phytopathology* 59:1641–5 (1969); Elliston, J., et al., "Induced Resistance to Anthracnose at a Distance from the Site of the Inducing Interaction," *Phytopathology* 61:1110–12 (1971); Skipp, R., et al., "Studies on Cross Protection in the Anthracnose Disease of Bean," *Physiological Plant Pathology* 3:299–313 (1973), which are hereby incorporated by reference), cultivar-pathogenic races attenuated by heat in host tissue prior to symptom appearance (Rahe, J. E., et al., "Metabolic Nature of the Infection-Limiting Effect of Heat on Bean Anthracnose," *Phytopathology* 60:1005–9 (1970), which is hereby incorporated by reference) or nonpathogens of bean. The anthracnose pathogen of cucumber, *Colletotrichum lagenarium*, was equally effective as non-pathogenic races as an inducer of systemic protection against all races of bean anthracnose. Protection was induced by *C. lagenarium* in cultivars resistant to one or more races of *C. lindemuthianum* as well as in cultivars susceptible to all reported races of the fungus and which accordingly had been referred to as 'lacking genetic resistance' to the pathogen (Elliston, J., et al., "Protection of Bean Against Anthracnose by Colletotrichum Species Nonpathogenic on Bean," *Phytopathologische Zeitschrift* 86:117–26 (1976); Elliston, J., et al., "A Comparative Study on the Development of Compatible, Incompatible and Induced Incompatible Interactions Between Collectotrichum Species and *Phaseolus Vulgaris*," *Phytopathologische Zeitschrift* 87:289–303 (1976), which are hereby incorporated by reference). These results suggest that the same mechanisms may be induced in cultivars reported as 'possessing' or 'lacking' resistance genes (Elliston, J., et al., "Relation of Phytoalexin Accumulation to Local and Systemic Protection of Bean Against Anthracnose," *Phytopathologische Zeitschrift* 88:114–30 (1977), which is hereby incorporated by reference). It also is apparent that cultivars susceptible to all races of *C. lindemuthianum* do not lack genes for resistance mechanisms against the pathogen.

Kuc, J., et al., "Protection of Cucumber Against *Colletotrichum lagenarium* by *Colletotrichum lagenarium*," *Physiological Plant Pathology* 7:195–9 (1975), which is hereby incorporated by reference), showed that cucumber plants could be systemically protected against disease caused by *Colletotrichum lagenarium* by prior inoculation of the cotyledons or the first true leaf with the same fungus. Subsequently, cucumbers have been systemically protected against fungal, bacterial, and viral diseases by prior localized infection with either fungi, bacteria, or viruses (Hammerschmidt, R., et al., "Protection of Cucumbers Against *Colletotrichum lagenarium* and *Cladosporium cucumerinum*," *Phytopathology* 66:790–3 (1976); Jenns, A. E., et al., "Localized Infection with Tobacco Necrosis Virus Protects Cucumber Against *Colletotrichum lagenarium*," *Physiological Plant Pathology* 11:207–12 (1977); Caruso, F. L., et al. "Induced Resistance of Cucumber to Anthracnose and Angular Leaf Spot by *Pseudomonas lachrymans* and *Colletotrichum Lagenarium*," *Physiological Plant Pathology* 14:191–201 (1979); Staub, T., et al., "Systemic Protection of Cucumber Plants Against Disease Caused by *Cladosporium cucumerinum* and *Colletotrichum lagenarium* by Prior Localized Infection with Either Fungus," *Physiological Plant Pathology*, 17:389–93 (1980); Bergstrom, G. C., et al., "Effects of Local Infection of Cucumber by *Colletotrichum lagenarium*, *Pseudomonas lachrymans* or Tobacco Necrosis Virus on Systemic Resistance to Cucumber Mosaic Virus," *Phytopathology* 72:922–6 (1982); Gessler, C., et al., "Induction of Resistance to Fusarium Wilt in Cucumber by Root and Foliar Pathogens," *Phytopathology* 72:1439–41 (1982); Basham, B., et al., "Tobacco Necrosis Virus Induces Systemic Resistance in Cucumbers Against *Sphaerotheca fuliginea*," *Physiological Plant Pathology* 23:137–44 (1983), which are hereby incorporated by reference). Nonspecific protection induced by infection with *C. lagenarium* or tobacco necrosis virus was effective against at least 13 pathogens, including obligatory and facultative parasitic fungi, local lesion and systemic viruses, wilt fungi, and bacteria. Similarly, protection was induced by and was also effective against root pathogens. Other curcurbits, including watermelon and muskmelon have been systemically protected against *C. lagenarium* (Caruso, F. L., et al., "Protection of Watermelon and Muskmelon Against *Colletotrichum lagenarium* by *Colletotrichum lagenarium*," *Phytopathology* 67:1285–9 (1977), which is hereby incorporated by reference).

Systemic protection in tobacco has also been induced against a wide variety of diseases (Kuc, J., et al., "Immunization for Disease Resistance in Tobacco," *Recent Advances in Tobacco Science* 9:179–213 (1983), which is hereby incorporated by reference). Necrotic lesions caused by tobacco mosaic virus enhanced resistance in the upper leaves to disease caused by the virus (Ross, A. F., et al., "Systemic Acquired Resistance Induced by Localized Virus Infections in Plants," *Virology* 14:340–58 (1961); Ross, A. F., et al., "Systemic Effects of Local Lesion Formation," *In: Viruses of Plants* pp. 127–50 (1966), which are hereby incorporated by reference). *Phytophthora parasitica* var. nicotianae, *P. tabacina* and *Pseudomonas tabaci* and reduced reproduction of the aphid *Myzus persicae* (McIntyre, J. L., et al., "Induction of Localized and Systemic Protection Against *Phytophthora Parasitica* var. nicotianae by Tobacco Mosaic Virus Infection of Tobacco Hypersensitive to the Virus," *Physiological Plant Pathology* 15:321–30 (1979); McIntyre, J. L., et al., "Effects of Localized Infections of *Nicotiana tabacum* by Tobacco Mosaic Virus on Systemic Resistance Against Diverse Pathogens and an Insect," *Phytopathology* 71:297–301 (1981), which are hereby incorporated by reference). Infiltration of heat-killed *P. tabaci* (Lovrekovich, L., et al., "Induced Reaction Against Wildfire Disease in Tobacco Leaves Treated with Heat-Killed Bacteria," *Nature* 205:823–4 (1965), which is hereby incorporated by reference), and *Pseudomonas solanacearum* (Sequeira, L., et al., "Interaction of Bacteria and Host Cell Walls: Its Relation to Mechanisms of Induced Resistance," *Physiological Plant Pathology* 10:43–50 (1977), which are hereby incorporated by reference), into tobacco leaves induced resistance against the same bacteria used for infiltration. Tobacco plants were also protected by the nematode *Pratylenchus penetrans* against *P. parasitica* var. nicotiana (McIntyre, J. L., et al. "Protection of Tobacco Against *Phytophthora parasitica* Var. Nicotianae by Cultivar-Nonpathogenic Races, Cell-Free Sonicates and *Pratylenchus Penetrans*," *Phytopathology* 68:235–9 (1978), which is hereby incorporated by reference).

Cruikshank, I. A. M., et al., "The Effect of Stem Infestation of Tobacco with *Peronospora tabacina* Adam on Foliage Reaction to Blue Mould," *Journal of the Australian Institute of Agricultural Science* 26:369–72 (1960), which is hereby incorporated by reference, were the first to report immunization of tobacco foliage against blue mould (i.e., *P. tabacina*) by stem injection with the fungus, which also involved dwarfing and premature senescence. It was recently discovered that injection external to the xylem not only alleviated stunting but also promoted growth and development. Immunized tobacco plants, in both glasshouse and field experiments, were approximately 40% taller, had a 40% increase in dry weight, 30% increase in fresh weight, and 4–6 more leaves than control plants (Tuzun, S., et al., "The Effect of Stem Injections with *Peronospora tabacina* and Metalaxyl Treatment on Growth of Tobacco and Protection Against Blue Mould in the Field," *Phytopathology* 74:804 (1984), which is hereby incorporated by reference). These plants flowered approximately 2–3 weeks earlier than control plants (Tuzun, S., et al., "Movement of a Factor in Tobacco Infected with *Peronospora tabacina* Adam which Systemically Protects Against Blue Mould," *Physiological Plant Pathology* 26:321–30 (1985), which is hereby incorporated by reference).

Systemic protection does not confer absolute immunity against infection, but reduces the severity of the disease and delays symptom development. Lesion number, lesion size, and extent of sporulation of fungal pathogens are all decreased. The diseased area may be reduced by more than 90%.

When cucumbers were given a 'booster' inoculation 3–6 weeks after the initial inoculation, immunization induced by *C. lagenarium* lasted through flowering and fruiting (Kuc, J., et al., "Aspects of the Protection of Cucumber Against *Colletotrichum lagenarium* by *Colletotrichum lagenarium*," *Phytopathology* 67:533–6 (1977), which is hereby incorporated by reference). Protection could not be induced once plants had set fruit. Tobacco plants were immunized for the growing season by stem injection with sporangia of *P. tabacina*. However, to prevent systemic blue mould development, this technique was only effective when the plants were above 20 cm in height.

Removal of the inducer leaf from immunized cucumber plants did not reduce the level of immunization of pre-existing expanded leaves. However, leaves which subsequently emerged from the apical bud were progressively less protected than their predecessors (Dean, R. A., et al., "Induced Systemic Protection in Cucumber: Time of Production and Movement of the 'Signal'," *Phytopathology* 76:966–70 (1986), which is hereby incorporated by reference). Similar results were reported by Ross, A. F., "Systemic Effects of Local Lesion Formation," *In: Viruses of Plants* pp. 127–50 (1966), which is hereby incorporated by reference, with tobacco (local lesion host) immunized against tobacco mosaic virus by prior infection with tobacco mosaic virus. In contrast, new leaves which emerged from scions excised from tobacco plants immunized by stem-injection with *P. tabacina* were highly protected (Tuzun, S., et al., "Transfer of Induced Resistance in Tobacco to Blue Mould (*Peronospora tabacina* Adam.) Via Callus," *Phytopathology* 75:1304 (1985), which is hereby incorporated by reference). Plants regenerated via tissue culture from leaves of immunized plants showed a significant reduction in blue mould compared to plants regenerated from leaves of non-immunized parents. Young regenerants only showed reduced sporulation. As plants aged, both lesion development and sporulation were reduced. Other investigators, however, did not reach the same conclusion, although a significant reduction in sporulation in one experiment was reported (Lucas, J. A., et al., "Nontransmissibility to Regenerants from Protected Tobacco Explants of Induced Resistance to *Peronospora hyoscyami*," *Phytopathology* 75:1222–5 (1985), which is hereby incorporated by reference).

Protection of cucumber and watermelon is effective in the glasshouse and in the field (Caruso, F. L., et al., "Field Protection of Cucumber Against *Colletotrichum lagenarium* by *C. Lagenarium*," *Phytopathology* 67:1290–2 (1977), which is hereby incorporated by reference). In one trial, the total lesion area of *C. lagenarium* on protected cucumber was less than 2% of the lesion areas on unprotected control plants. Similarly, only 1 of 66 protected, challenged plants died, whereas 47 of 69 unprotected, challenged watermelons died. In extensive field trials in Kentucky and Puerto Rico, stem injection of tobacco with sporangia of *P. tabacina* was at least as effective in controlling blue mould as the best fungicide, metalaxyl. Plants were protected 95–99%, based on the necrotic area and degree of sporulation, leading to a yield increase of 10–25% in cured tobacco.

Induced resistance against bacteria and viruses appears to be expressed as suppression of disease symptoms or pathogen multiplication or both (Caruso, F. L., et al., "Induced Resistance of Cucumber to Anthracnose and Angular Leaf Spot by *Pseudomonas lachrymans* and *Colletotrichum lagenarium*," *Physiological Plant Pathology* 14:191–201 (1979); Doss, M., et al., "Systemic Acquired Resistance of Cucumber to *Pseudomonas lachrymans* as Expressed in Suppression of Symptoms, but not in Multiplication of Bacteria," *Acta Phytopathologia Academiae Scientiarum Hungaricae* 16:(3–4), 269–72 (1981); Jenns, A. E., et al., "Non-Specific Resistance to Pathogens Induced Systemically by Local Infection of Cucumber with Tobacco Necrosis Virus, *Colletotrichum lagenarium* or *Pseudomonas lachrymans*," *Phytopathologia mediterranea* 18:129–34 (1979), which are hereby incorporated by reference).

As described above, research concerning systemic acquired resistance involves infecting plants with infectious pathogens. Although studies in this area are useful in understanding how systemic acquired resistance works, eliciting such resistance with infectious agents is not commercially useful, because such plant-pathogen contact can weaken or kill plants. The present invention is directed to overcoming this deficiency.

SUMMARY OF THE INVENTION

The present invention relates to a method of imparting pathogen resistance to plants. This method involves applying a hypersensitive response elicitor polypeptide or protein in a non-infectious form to a plant under conditions where the polypeptide or protein contacts cells of the plant.

Another aspect of the present invention relates to a pathogen-resistant plant with cells in contact with non-infectious hypersensitive response elicitor polypeptide or protein.

Yet another aspect of the present invention relates to a composition for imparting pathogen resistance to plants. The composition includes a non-infectious, hypersensitive response elicitor polypeptide or protein and a carrier.

The present invention has the potential to: treat plant diseases which were previously untreatable; treat diseases systemically that one would not want to treat separately due to cost; and avoid the use of infectious agents to treat diseases. The present invention can impart resistance without using agents pathogenic to the plants being treated or to plants situated nearby those treated. Since the present invention involves use of a natural product that is fully biodegradable, the environment would not be contaminated.

Figure 1:
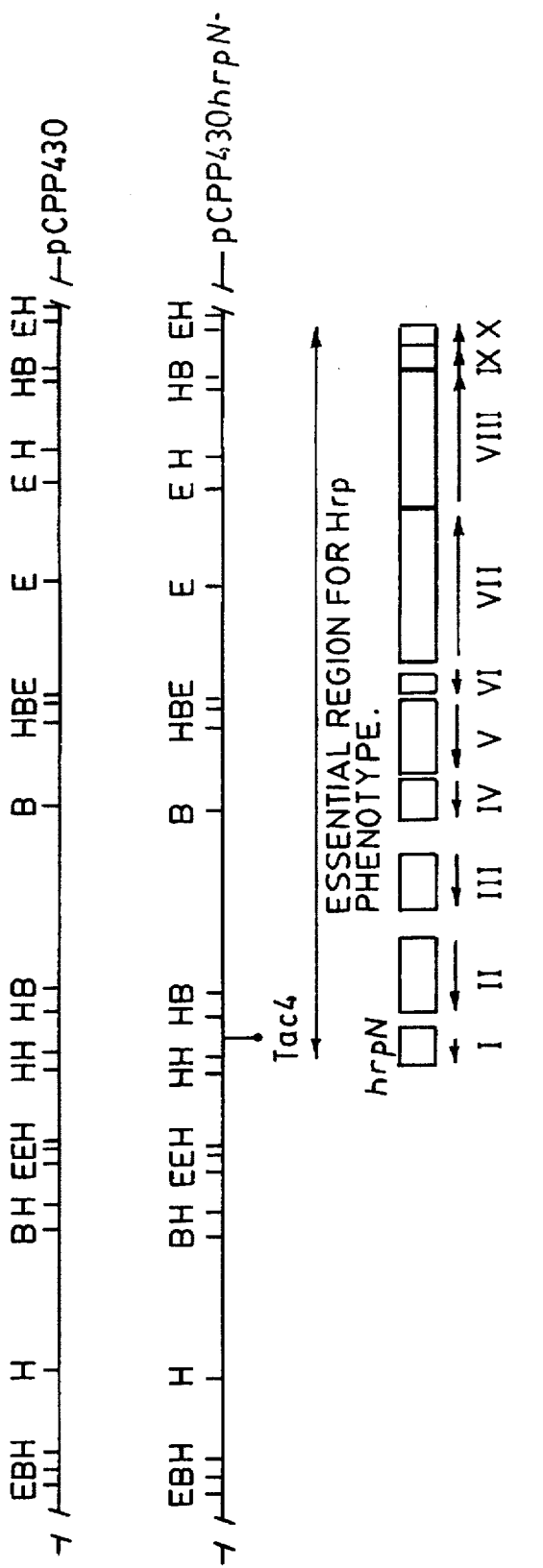
FIG. 1 shows the genetic organization of the gene cluster encoding the hypersensitive response elicitor polypeptide or protein for *Erwinia amylovora* (i.e. hrpN). The top line shows the restriction enzyme map of plasmid vector pCPP430, where E=Eco RI, B=Bam HI, and H=Hind III. The rectangles represent transcriptional units, and the arrows under the rectangles indicate the directions of transcription. The bigger arrow indicates the region necessary for ultimate translation of the hypersensitive response elicitor polypeptide or protein. pCPP430 hrpn is the derivative of pCPP430 in which hrpN is mutated by the insertion of transposor TnStac.

FIG. 2 is a map of plasmid vector pCPP9. Significant features are the mobilization (mob) site for conjugation; the cohesive site of λ (cos); and the partition region (par) for stable inheritance of the plasmid. B, BamHI; E, EcoRI; H, HindIII; P, PstI; S, SalI; Sm, SmaI; oriV, origin of replication; Spr, spectinomycin resistance; Smr, streptomycin resistance.

DETAILED DESCRIPTION OF THE INVENTION

The present invention relates to a method of imparting pathogen resistance to plants. This method involves applying a hypersensitive response elicitor polypeptide or protein in a non-infectious form to all or part of a plant under conditions where the polypeptide or protein contacts all or part of the cells of the plant.

Another aspect of the present invention relates to a pathogen-resistant plant with cells in contact with a non-infectious hypersensitive response elicitor polypeptide or protein.

Yet another aspect of the present invention relates to a composition for imparting pathogen resistance to plants. The composition includes a non-infectious hypersensitive response elicitor polypeptide or protein and a carrier.

The hypersensitive response elicitor polypeptide or protein utilized in the present invention can correspond to hypersensitive response elicitor polypeptides or proteins derived from a wide variety of pathogens. Such polypeptides or proteins are able to elicit local necrosis in plant tissue contacted by the elicitor. Preferred pathogens include *Erwinia amylovora, Erwinia chrysanthemi, Pseudomonas syringae, Pseudomonas solancearum, Xanthomonas campestris,* or mixtures thereof.

For purposes of the present invention, non-infectious forms of the hypersensitive response elicitor polypeptide or protein can induce a hypersensitive response without causing disease in the plant with which the polypeptide or protein is contacted. This can be achieved in a number of ways, including: 1) application of an isolated elicitor polypeptide or protein; 2) application of bacteria which do not cause disease and are transformed with genes encoding a hypersensitive response elicitor polypeptide or protein; and 3) application of bacteria which cause disease in some plant species (but not in those to which they are applied) and naturally contain a gene encoding the hypersensitive response elicitor polypeptide or protein.

In one embodiment of the present invention, the hypersensitive response elicitor polypeptides or proteins can be isolated from their corresponding organisms and applied to plants. Such isolation procedures are well known, as described in Arlat, M., F. Van Gijsegem, J. C. Huet, J. C. Pemollet, and C. A. Boucher, "PopA1, a Protein which Induces a Hypersensitive-like Response in Specific Petunia Genotypes is Secreted via the Hrp Pathway of *Pseudomonas solanacearum,*" *EMBO J.* 13:543–553 (1994); He, S. Y., H. C. Huang, and A. Collmer, "*Pseudomonas syringae* pv. syringae Harpin$_{Pss}$: a Protein that is Secreted via the Hrp Pathway and Elicits the Hypersensitive Response in Plants," *Cell* 73:1255–1266 (1993); and Wei, Z.-M., R. J. Laby, C. H. Zumoff, D. W. Bauer, S.-Y. He, A. Collmer, and S. V. Beer, "Harpin Elicitor of the Hypersensitive Response Produced by the Plant Pathogen *Erwinia amylovora, Science* 257:85–88 (1992), which are hereby incorporated by reference. See also pending U.S. patent application Ser. Nos. 08/200,024 and 08/062,024, which are hereby incorporated by reference. Preferably, however, the isolated hypersensitive response elicitor polypeptides or proteins of the present invention are produced recombinantly and purified as described below.

In other embodiments of the present invention, the hypersensitive response elicitor polypeptide or protein of the present invention can be applied to plants by applying bacteria containing genes encoding the hypersensitive response elicitor polypeptide or protein. Such bacteria must be capable of secreting or exporting the polypeptide or protein so that the elicitor can contact plant cells. In these embodiments, the hypersensitive response elicitor polypeptide or protein is produced by the bacteria in planta or just prior to introduction of the bacteria to the plants.

In one embodiment of the bacterial application mode of the present invention, the bacteria do not cause the disease and have been transformed (e.g., recombinantly) with genes encoding a hypersensitive response elicitor polypeptide or protein. For example, *E. coli*, which do not elicit a hypersensitive response in plants, can be transformed with genes encoding a hypersensitive response elicitor polypeptide or protein and then applied to plants. Bacterial species (other than *E. coli*) can also be used in this embodiment of the present invention.

In another embodiment of the bacterial application mode of the present invention, the bacteria do cause disease and naturally contain a gene encoding a hypersensitive response elicitor polypeptide or protein. Examples of such bacteria are noted above. However, in this embodiment these bacteria are applied to plants which are not susceptible to the disease carried by the bacteria. For example, *Erwinia amylovora* causes disease in apple or pear but not in tomato. However, such bacteria will elicit a hypersensitive response in tomato. Accordingly, in accordance with this embodiment of the present invention, *Erwinia amylovora* can be applied to tomato to impart pathogen resistance without causing disease in that species.

The hypersensitive response elicitor polypeptide or protein from *Erwinia chrysanthemi* has an amino acid sequence corresponding to SEQ. ID. No. 1 as follows:

Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
                20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
        50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
                100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
        130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
                180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
        210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
                260                 265                 270

Pro Asp Asp Asp Gly Met Thr Gly Ala Ser Met Asp Lys Phe Arg Gln
                275                 280                 285

Ala Met Gly Met Ile Lys Ser Ala Val Ala Gly Asp Thr Gly Asn Thr
        290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                  325              330              335

Asn Ala

This hypersensitive response elicitor polypeptide or protein has a molecular weight of 34 kDa, is heat stable, has a glycine content of greater than 16%, and contains substantially no cysteine. The *Erwinia chrysanthemi* hypersensitive response elicitor polypeptide or protein is encoded by a DNA molecule having a nucleotide sequence corresponding to SEQ. ID. No. 2 as follows:

| | | | | | | |
|---|---|---|---|---|---|---|
| CGATTTTACC | CGGGTGAACG | TGCTATGACC | GACAGCATCA | CGGTATTCGA | CACCGTTACG | 60 |
| GCGTTTATGG | CCGCGATGAA | CCGGCATCAG | GCGGCGCGCT | GGTCGCCGCA | ATCCGGCGTC | 120 |
| GATCTGGTAT | TTCAGTTTGG | GGACACCGGG | CGTGAACTCA | TGATGCAGAT | TCAGCCGGGG | 180 |
| CAGCAATATC | CCGGCATGTT | GCGCACGCTG | CTCGCTCGTC | GTTATCAGCA | GGCGGCAGAG | 240 |
| TGCGATGGCT | GCCATCTGTG | CCTGAACGGC | AGCGATGTAT | TGATCCTCTG | GTGGCCGCTG | 300 |
| CCGTCGGATC | CCGGCAGTTA | TCCGCAGGTG | ATCGAACGTT | TGTTTGAACT | GGCGGGAATG | 360 |
| ACGTTGCCGT | CGCTATCCAT | AGCACCGACG | GCGCGTCCGC | AGACAGGGAA | CGGACGCGCC | 420 |
| CGATCATTAA | GATAAAGGCG | GCTTTTTTTA | TTGCAAAACG | GTAACGGTGA | GGAACCGTTT | 480 |
| CACCGTCGGC | GTCACTCAGT | AACAAGTATC | CATCATGATG | CCTACATCGG | GATCGGCGTG | 540 |
| GGCATCCGTT | GCAGATACTT | TTGCGAACAC | CTGACATGAA | TGAGGAAACG | AAATTATGCA | 600 |
| AATTACGATC | AAAGCGCACA | TCGGCGGTGA | TTTGGGCGTC | TCCGGTCTGG | GGCTGGGTGC | 660 |
| TCAGGGACTG | AAAGGACTGA | ATTCCGCGGC | TTCATCGCTG | GGTTCCAGCG | TGGATAAACT | 720 |
| GAGCAGCACC | ATCGATAAGT | TGACCTCCGC | GCTGACTTCG | ATGATGTTTG | GCGGCGCGCT | 780 |
| GGCGCAGGGG | CTGGGCGCCA | GCTCGAAGGG | GCTGGGGATG | AGCAATCAAC | TGGGCCAGTC | 840 |
| TTTCGGCAAT | GGCGCGCAGG | GTGCGAGCAA | CCTGCTATCC | GTACCGAAAT | CCGGCGGCGA | 900 |
| TGCGTTGTCA | AAAATGTTTG | ATAAAGCGCT | GGACGATCTG | CTGGGTCATG | ACACCGTTGAC | 960 |
| CAAGCTGACT | AACCAGAGCA | ACCAACTGGC | TAATTCAATG | CTGAACGCCA | GCCAGATGAC | 1020 |
| CCAGGGTAAT | ATGAATGCGT | TCGGCAGCGG | TGTGAACAAC | GCACTGTCGT | CCATTCTCGG | 1080 |
| CAACGGTCTC | GGCCAGTCGA | TGAGTGGCTT | CTCTCAGCCT | TCTCTGGGGG | CAGGCGGCTT | 1140 |
| GCAGGGCCTG | AGCGGCGCGG | GTGCATTCAA | CCAGTTGGGT | AATGCCATCG | GCATGGGCGT | 1200 |
| GGGGCAGAAT | GCTGCGCTGA | GTGCGTTGAG | TAACGTCAGC | ACCCACGTAG | ACGGTAACAA | 1260 |
| CCGCCACTTT | GTAGATAAAG | AAGATCGGCC | CATGGCGATG | GCC | AGTTTATGGA | 1320 |
| TCAGTATCCG | GAAATATTCG | GTAAACCGGA | ATACCAGAAA | GATGGCTGGA | GTTCGCCGAA | 1380 |
| GACGGACGAC | AAATCCTGGG | CTAAAGCGCT | GAGTAAACCG | GATGATGACG | GTATGACCGG | 1440 |
| CGCCAGCATG | GACAAATTCC | GTCAGGCGAT | GGGTATGATC | AAAAGCGCGG | TGGCGGGTGA | 1500 |
| TACCGGCAAT | ACCAACCTGA | ACCTGCGTGG | CGCGGGCGGT | GCATCGCTGG | GTATCGATGC | 1560 |
| GGCTGTCGTC | GGCGATAAAA | TAGCCAACAT | GTCGCTGGGT | AAGCTGGCCA | ACGCCTGATA | 1620 |
| ATCTGTGCTG | GCCTGATAAA | GCGGAAACGA | AAAAAGAGAC | GGGGAAGCCT | GTCTCTTTTC | 1680 |
| TTATTATGCG | GTTTATGCGG | TTACCTGGAC | CGGTTAATCA | TCGTCATCGA | TCTGGTACAA | 1740 |
| ACGCACATTT | TCCCGTTCAT | TCGCGTCGTT | ACGCGCCACA | ATCGGGATGG | CATCTTCCTC | 1800 |
| GTCGCTCAGA | TTGCGCGGCT | GATGGGGAAC | GCCGGGTGGA | ATATAGAGAA | ACTCGCCGGC | 1860 |
| CAGATGGAGA | CACGTCTGCG | ATAAATCTGT | GCCGTAACGT | GTTTCTATCC | GCCCCTTTAG | 1920 |
| CAGATAGATT | GCGGTTTCGT | AATCAACATG | GTAATGCGGT | TCCGCCTGTG | CGCCGGCCGG | 1980 |
| GATCACCACA | ATATTCATAG | AAAGCTGTCT | TGCACCTACC | GTATCGCGGG | AGATACCGAC | 2040 |
| AAAATAGGGC | AGTTTTTGCG | TGGTATCCGT | GGGGTGTTCC | GGCCTGACAA | TCTTGAGTTG | 2100 |
| GTTCGTCATC | ATCTTTCTCC | ATCTGGGCGA | CCTGATCGGT | T | | 2141 |

The hypersensitive response elicitor polypeptide or protein derived from *Erwinia amylovora* has an amino acid sequence corresponding to SEQ. ID. No. 3 as follows:

Met Ser Leu Asn Thr Ser Gly Leu Gly Ala Ser Thr Met Gln Ile Ser
1                5              10              15

Ile Gly Ala Gly Gly Asn Asn Gly Leu Leu Gly Thr Ser Arg Gln
          20              25              30

Asn Ala Gly Leu Gly Gly Asn Ser Ala Leu Gly Leu Gly Gly Asn
        35              40              45

Gln Asn Asp Thr Val Asn Gln Leu Ala Gly Leu Leu Thr Gly Met Met
      50              55              60

Met Met Met Ser Met Met Gly Gly Gly Leu Met Gly Gly Gly Leu
65              70              75              80

Gly Gly Gly Leu Gly Asn Leu Gly Gly Ser Gly Gly Leu Gly Glu
            85              90              95

Gly Leu Ser Asn Ala Leu Asn Asp Met Leu Gly Gly Ser Leu Asn Thr
          100              105              110

Leu Gly Ser Lys Gly Gly Asn Asn Thr Thr Ser Thr Thr Asn Ser Pro
        115              120              125

Leu Asp Gln Ala Leu Gly Ile Asn Ser Thr Ser Gln Asn Asp Asp Ser
      130              135              140

Thr Ser Gly Thr Asp Ser Thr Ser Asp Ser Ser Asp Pro Met Gln Gln
145              150              155              160

Leu Leu Lys Met Phe Ser Glu Ile Met Gln Ser Leu Phe Gly Asp Gly
          165              170              175

Gln Asp Gly Thr Gln Gly Ser Ser Ser Gly Gly Lys Gln Pro Thr Glu
        180              185              190

Gly Glu Gln Asn Ala Tyr Lys Lys Gly Val Thr Asp Ala Leu Ser Gly
      195              200              205

Leu Met Gly Asn Gly Leu Ser Gln Leu Leu Gly Asn Gly Leu Gly
      210              215              220

Gly Gly Gln Gly Gly Asn Ala Gly Thr Gly Leu Asp Gly Ser Ser Leu
225              230              235              240

Gly Gly Lys Gly Leu Gln Asn Leu Ser Gly Pro Val Asp Tyr Gln Gln
          245              250              255

Leu Gly Asn Ala Val Gly Thr Gly Ile Gly Met Lys Ala Gly Ile Gln
        260              265              270

-continued

| | | | | | | | | | | | | |
|---|---|---|---|---|---|---|---|---|---|---|---|---|
| Ala | Leu | Asn | Asp | Ile | Gly | Thr | His | Arg | His | Ser | Ser | Thr | Arg | Ser | Phe |
| | | | 275 | | | | 280 | | | | 285 | | | | |

Val Asn Lys Gly Asp Arg Ala Met Ala Lys Glu Ile Gly Gln Phe Met
290           295             300

Asp Gln Tyr Pro Glu Val Phe Gly Lys Pro Gln Tyr Gln Lys Gly Pro
305             310             315             320

Gly Gln Glu Val Lys Thr Asp Asp Lys Ser Trp Ala Lys Ala Leu Ser
325             330             335

Lys Pro Asp Asp Asp Gly Met Thr Pro Ala Ser Met Glu Gln Phe Asn
340             345             350

Lys Ala Lys Gly Met Ile Lys Arg Pro Met Ala Gly Asp Thr Gly Asn
355             360             365

Gly Asn Leu Gln His Ala Val Pro Val Val Leu Arg Trp Val Leu Met
370             375             380

Pro
385

This hypersensitive response elicitor polypeptide or protein has a molecular weight of about 37 kDa, it has a pI of approximately 4.3, and is heat stable at 100° C. for at least 10 minutes. This hypersensitive response elicitor polypeptide or protein has substantially no cysteine. The hypersensitive response elicitor polypeptide or protein derived from *Erwinia amylovora* is more fully described in Wei, Z.-M., R. J. Laby, C. H. Zumoff, D. W. Bauer, S.-Y. He, A. Collmer, and S. V. Beer, "Harpin, Elicitor of the Hypersensitive Response Produced by the Plant Pathogen *Erwinia amylovora*," *Science* 257:85–88 (1992), which is hereby incorporated by reference. The DNA molecule encoding this polypeptide or protein has a nucleotide sequence corresponding to SEQ. ID. No. 4 as follows:

| | | | | | | |
|---|---|---|---|---|---|---|
| ATGAGTCTGA | ATACAAGTGG | GCTGGGAGCG | TCAACGATGC | AAATTTCTAT | CGGCGGTGCG | 60 |
| GGCGGAAATA | ACGGGTTGCT | GGGTACCAGT | CGCCAGAATG | CTGGGTTGGG | TGGCAATTCT | 120 |
| GCACTGGGGC | TGGGCGGCGG | TAATCAAAAT | GATACCGTCA | ATCAGCTGGC | TGGCTTACTC | 180 |
| ACCGGCATGA | TGATGATGAT | GAGCATGATG | GGCGGTGGTG | GGCTGATGGG | CGGTGGCTTA | 240 |
| GGCGGTGGCT | TAGGTAATGG | CTTGGGTGGC | TCAGGTGGCC | TGGGCGAAGG | ACTGTCGAAC | 300 |
| GCGCTGAACG | ATATGTTAGG | CGGTTCGCTG | AACACGCTGG | GCTCGAAAGG | CGGCAACAAT | 360 |
| ACCACTTCAA | CAACAAATTC | CCCGCTGGAC | CAGGCGCTGG | GTATTAACTC | AACGTCCCAA | 420 |
| AACGACGATT | CCACCTCCGG | CACAGATTCC | ACCTCAGACT | CCAGCGACCC | GATGCAGCAG | 480 |
| CTGCTGAAGA | TGTTCAGCGA | GATAATGCAA | AGCCTGTTTG | GTGATGGGCA | AGATGGCACC | 540 |
| CAGGGCAGTT | CCTCTGGGGG | CAAGCAGCCG | ACCGAAGGCG | AGCAGAACGC | CTATAAAAAA | 600 |
| GGAGTCACTG | ATGCGCTGTC | GGGCCTGATG | GGTAATGGTC | TGAGCCAGCT | CCTTGGCAAC | 660 |
| GGGGGACTGG | GAGGTGGTCA | GGGCGGTAAT | GCTGGCACGG | GTCTTGACGG | TTCGTCGCTG | 720 |
| GGCGGCAAAG | GGCTGCAAAA | CCTGAGCGGG | CCGGTGGACT | ACCAGCAGTT | AGGTAACGCC | 780 |
| GTGGGTACCG | GTATCGGTAT | GAAAGCGGGC | ATTCAGGCGC | TGAATGATAT | CGGTACGCAC | 840 |
| AGGCACAGTT | CAACCCGTTC | TTTCGTCAAT | AAAGGCGATC | GGGCGATGGC | GAAGGAAATC | 900 |
| GGTCAGTTCA | TGGACCAGTA | TCCTGAGGTG | TTTGGCAAGC | CGCAGTACCA | GAAAGGCCCG | 960 |
| GGTCAGGAGG | TGAAAACCGA | TGACAAATCA | TGGGCAAAAG | CACTGAGCAA | GCCAGATGAC | 1020 |
| GACGGAATGA | CACCAGCCAG | TATGGAGCAG | TTCAACAAAG | CCAAGGGCAT | GATCAAAAGG | 1080 |
| CCCATGGCGG | GTGATACCGG | CAACGGCAAC | CTGCAGCACG | CGGTGCCGGT | GGTTCTTCGC | 1140 |
| TGGGTATTGA | TGCCATGA | | | | | 1158 |

The hypersensitive response elicitor polypeptide or protein derived from *Pseudomonas syringae* has an amino acid sequence corresponding to SEQ. ID. No. 5 as follows:

| | | | | | | | | | | | | | | | |
|---|---|---|---|---|---|---|---|---|---|---|---|---|---|---|---|
| Met | Gln | Ser | Leu | Ser | Leu | Asn | Ser | Ser | Ser | Leu | Gln | Thr | Pro | Ala | Met |
| 1 | | | | 5 | | | | | 10 | | | | | 15 | |
| Ala | Leu | Val | Leu | Val | Arg | Pro | Glu | Ala | Glu | Thr | Thr | Gly | Ser | Thr | Ser |
| | | | 20 | | | | | 25 | | | | | 30 | | |
| Ser | Lys | Ala | Leu | Gln | Glu | Val | Val | Val | Lys | Leu | Ala | Glu | Glu | Leu | Met |
| | | 35 | | | | | 40 | | | | | 45 | | | |
| Arg | Asn | Gly | Gln | Leu | Asp | Asp | Ser | Ser | Pro | Leu | Gly | Lys | Leu | Leu | Ala |
| | 50 | | | | | 55 | | | | | 60 | | | | |
| Lys | Ser | Met | Ala | Ala | Asp | Gly | Lys | Ala | Gly | Gly | Gly | Ile | Glu | Asp | Val |
| 65 | | | | | 70 | | | | | 75 | | | | | 80 |
| Ile | Ala | Ala | Leu | Asp | Lys | Leu | Ile | His | Glu | Lys | Leu | Gly | Asp | Asn | Phe |
| | | | | 85 | | | | | 90 | | | | | 95 | |
| Gly | Ala | Ser | Ala | Asp | Ser | Ala | Ser | Gly | Thr | Gly | Gln | Gln | Asp | Leu | Met |
| | | | 100 | | | | | 105 | | | | | 110 | | |
| Thr | Gln | Val | Leu | Asn | Gly | Leu | Ala | Lys | Ser | Met | Leu | Asp | Asp | Leu | Leu |
| | | 115 | | | | | 120 | | | | | 125 | | | |

-continued

| | | | | | | | | | | | | | | |
|---|---|---|---|---|---|---|---|---|---|---|---|---|---|---|
| Thr | Lys 130 | Gln | Asp | Gly | Gly | Thr 135 | Ser | Phe | Ser | Glu | Asp 140 | Met | Pro | Met |
| Leu 145 | Asn | Lys | Ile | Ala | Gln 150 | Phe | Met | Asp | Asp | Asn 155 | Pro | Ala | Gln | Phe | Pro 160 |
| Lys | Pro | Asp | Ser | Gly 165 | Ser | Trp | Val | Asn | Glu 170 | Leu | Lys | Glu | Asp | Asn 175 | Phe |
| Leu | Asp | Gly | Asp 180 | Glu | Thr | Ala | Ala | Phe 185 | Arg | Ser | Ala | Leu | Asp 190 | Ile | Ile |
| Gly | Gln | Gln 195 | Leu | Gly | Asn | Gln | Gln 200 | Ser | Asp | Ala | Gly | Ser 205 | Leu | Ala | Gly |
| Thr | Gly 210 | Gly | Gly | Leu | Gly | Thr 215 | Pro | Ser | Ser | Phe | Ser 220 | Asn | Asn | Ser | Ser |
| Val 225 | Met | Gly | Asp | Pro | Leu 230 | Ile | Asp | Ala | Asn | Thr 235 | Gly | Pro | Gly | Asp | Ser 240 |
| Gly | Asn | Thr | Arg | Gly 245 | Glu | Ala | Gly | Gln | Leu 250 | Ile | Gly | Glu | Leu | Ile 255 | Asp |
| Arg | Gly | Leu | Gln 260 | Ser | Val | Leu | Ala | Gly 265 | Gly | Gly | Leu | Gly | Thr 270 | Pro | Val |
| Asn | Thr | Pro 275 | Gln | Thr | Gly | Thr | Ser 280 | Ala | Asn | Gly | Gly | Gln 285 | Ser | Ala | Gln |
| Asp | Leu 290 | Asp | Gln | Leu | Leu | Gly 295 | Gly | Leu | Leu | Leu | Lys 300 | Gly | Leu | Glu | Ala |
| Thr 305 | Leu | Lys | Asp | Ala | Gly 310 | Gln | Thr | Gly | Thr | Asp 315 | Val | Gln | Ser | Ser | Ala 320 |
| Ala | Gln | Ile | Ala | Thr 325 | Leu | Leu | Val | Ser | Thr 330 | Leu | Leu | Gln | Gly | Thr 335 | Arg |
| Asn | Gln | Ala | Ala 340 | Ala | | | | | | | | | | | |

This hypersensitive response elicitor polypeptide or protein has a molecular weight of 34–35 kDa. It is rich in glycine (about 13.5%) and lacks cysteine and tyrosine. Further information about the hypersensitive response elicitor derived from *Pseudomonas syringae* is found in He, S. Y., H. C. Huang, and A. Collmer, "*Pseudomonas syringae* pv. syringae Harpinp$_{Pss}$: a Protein that is Secreted via the Hrp Pathway and Elicits the Hypersensitive Response in Plants," *Cell* 73:1255–1266 (1993), which is hereby incorporated by reference. The DNA molecule encoding the hypersensitive response elicitor from *Pseudomonas syringae* has a nucleotide sequence corresponding to SEQ. ID. No. 6 as follows:

| | | | | | | |
|---|---|---|---|---|---|---|
| ATGCAGAGTC | TCAGTCTTAA | CAGCAGCTCG | CTGCAAACCC | CGGCAATGGC | CCTTGTCCTG | 60 |
| GTACGTCCTG | AAGCCGAGAC | GACTGGCAGT | ACGTCGAGCA | AGGCGCTTCA | GGAAGTTGTC | 120 |
| GTGAAGCTGG | CCGAGGAACT | GATGCGCAAT | GGTCAACTCG | ACGACAGCTC | GCCATTGGGA | 180 |
| AAACTGTTGG | CCAAGTCGAT | GGCCGCAGAT | GGCAAGGCGG | GCGGCGGTAT | TGAGGATGTC | 240 |
| ATCGCTGCGC | TGGACAAGCT | GATCCATGAA | AAGCTCGGTG | ACAACTTCGG | CGCGTCTGCG | 300 |
| GACAGCGCCT | CGGGTACCGG | ACAGCAGGAC | CTGATGACTC | AGGTGCTCAA | TGGCCTGGCC | 360 |
| AAGTCGATGC | TCGATGATCT | TCTGACCAAG | CAGGATGGCG | GGACAAGCTT | CTCCGAAGAC | 420 |
| GATATGCCGA | TGCTGAACAA | GATCGCGCAG | TTCATGGATG | ACAATCCCGC | ACAGTTTCCC | 480 |
| AAGCCGGACT | CGGGCTCCTG | GGTGAACGAA | CTCAAGGAAG | ACAACTTCCT | TGATGGCGAC | 540 |
| GAAACGGCTG | CGTTCCGTTC | GGCACTCGAC | ATCATTGGCC | AGCAACTGGG | TAATCAGCAG | 600 |
| AGTGACGCTG | GCAGTCTGCC | AGGGACGGGT | GGAGGTCTGG | GCACTCCGAG | CAGTTTTTCC | 660 |
| AACAACTCGT | CCGTGATGGG | TGATCCGCTG | ATCGACGCCA | ATACCGGTCC | CGGTGACAGC | 720 |
| GGCAATACCC | GTGGTGAAGC | GGGGCAACTG | ATCGGCGAGC | TTATCGACCG | TGGCCTGCAA | 780 |
| TCGGTATTGG | CCGGTGGTGG | ACTGGGCACA | CCCGTAAACA | CCCCGCAGAC | CGGTACGTCG | 840 |
| GCGAATGGCG | GACAGTCCGC | TCAGGATCTT | GATCAGTTGC | TGGGCGGCTT | GCTGCTCAAG | 900 |
| GGCCTGGAGG | CAACGCTCAA | GGATGCCGGG | CAAACAGGCA | CCGACGTGCA | GTCGAGCGCT | 960 |
| GCGCAAATCG | CCACCTTGCT | GGTCAGTACG | CTGCTGCAAG | GCACCCGCAA | TCAGGCTGCA | 1020 |
| GCCTGA | | | | | | 1026 |

The hypersensitive response elicitor polypeptide or protein derived from *Pseudomonas solanacearum* has an amino acid sequence corresponding to SEQ. ID. No. 7 as follows:

| | | | | | | | | | | | | | | |
|---|---|---|---|---|---|---|---|---|---|---|---|---|---|---|
| Met 1 | Ser | Val | Gly | Asn 5 | Ile | Gln | Ser | Pro | Ser 10 | Asn | Leu | Pro | Gly | Leu 15 | Gln |

-continued

| Asn | Leu | Asn | Leu 20 | Asn | Thr | Asn | Thr | Asn 25 | Ser | Gln | Gln | Ser | Gly 30 | Gln | Ser |
| --- | --- | --- | --- | --- | --- | --- | --- | --- | --- | --- | --- | --- | --- | --- | --- |
| Val | Gln | Asp 35 | Leu | Ile | Lys | Gln | Val 40 | Glu | Lys | Asp | Ile | Leu 45 | Asn | Ile | Ile |
| Ala | Ala 50 | Leu | Val | Gln | Lys | Ala 55 | Ala | Gln | Ser | Ala | Gly 60 | Gly | Asn | Thr | Gly |
| Asn 65 | Thr | Gly | Asn | Ala | Pro 70 | Ala | Lys | Asp | Gly | Asn 75 | Ala | Asn | Ala | Gly | Ala 80 |
| Asn | Asp | Pro | Ser | Lys 85 | Asn | Asp | Pro | Ser | Lys 90 | Ser | Gln | Ala | Pro | Gln 95 | Ser |
| Ala | Asn | Lys | Thr 100 | Gly | Asn | Val | Asp | Asp 105 | Ala | Asn | Asn | Gln | Asp 110 | Pro | Met |
| Gln | Ala | Leu 115 | Met | Gln | Leu | Leu | Glu 120 | Asp | Leu | Val | Lys | Leu 125 | Leu | Lys | Ala |
| Ala | Leu 130 | His | Met | Gln | Gln | Pro 135 | Gly | Gly | Asn | Asp | Lys 140 | Gly | Asn | Gly | Val |
| Gly 145 | Gly | Ala | Asn | Gly | Ala 150 | Lys | Gly | Ala | Gly | Gly 155 | Gln | Gly | Gly | Leu | Ala 160 |
| Glu | Ala | Leu | Gln | Glu 165 | Ile | Glu | Gln | Ile | Leu 170 | Ala | Gln | Leu | Gly | Gly 175 | Gly |
| Gly | Ala | Gly | Ala 180 | Gly | Ala | Gly | Gly 185 | Gly | Val | Gly | Gly | Ala 190 | Gly | Gly |
| Ala | Asp | Gly 195 | Gly | Ser | Gly | Ala | Gly 200 | Gly | Ala | Gly | Gly | Ala 205 | Asn | Gly | Ala |
| Asp | Gly 210 | Gly | Asn | Gly | Val | Asn 215 | Gly | Asn | Gln | Ala | Asn 220 | Gly | Pro | Gln | Asn |
| Ala 225 | Gly | Asp | Val | Asn | Gly 230 | Ala | Asn | Gly | Ala | Asp 235 | Asp | Gly | Ser | Glu | Asp 240 |
| Gln | Gly | Gly | Leu | Thr 245 | Gly | Val | Leu | Gln | Lys 250 | Leu | Met | Lys | Ile | Leu 255 | Asn |
| Ala | Leu | Val | Gln 260 | Met | Met | Gln | Gln | Gly 265 | Gly | Leu | Gly | Gly | Gly 270 | Asn | Gln |
| Ala | Gln | Gly 275 | Gly | Ser | Lys | Gly | Ala 280 | Gly | Asn | Ala | Ser | Pro 285 | Ala | Ser | Gly |
| Ala | Asn 290 | Pro | Gly | Ala | Asn | Gln 295 | Pro | Gly | Ser | Ala | Asp 300 | Asp | Gln | Ser | Ser |
| Gly 305 | Gln | Asn | Asn | Leu | Gln 310 | Ser | Gln | Ile | Met | Asp 315 | Val | Val | Lys | Glu | Val 320 |
| Val | Gln | Ile | Leu | Gln 325 | Gln | Met | Leu | Ala | Ala 330 | Gln | Asp | Gly | Gly | Ser 335 | Gln |
| Gln | Ser | Thr | Ser 340 | Thr | Gln | Pro | Met | | | | | | | | |

It is encoded by a DNA molecule having a nucleotide sequence corresponding SEQ. ID. No. 8 as follows:

| | | | | | | |
|---|---|---|---|---|---|---|
| ATGTCAGTCG | GAAACATCCA | GAGCCCGTCG | AACCTCCCGG | GTCTGCAGAA | CCTGAACCTC | 60 |
| AACACCAACA | CCAACAGCCA | GCAATCGGGC | CAGTCCGTGC | AAGACCTGAT | CAAGCAGGTC | 120 |
| GAGAAGGACA | TCCTCAACAT | CATCGCAGCC | CTCGTGCAGA | AGGCCGCACA | GTCGGCGGGC | 180 |
| GGCAACACCG | GTAACACCGG | CAACGCGCCG | GCGAAGGACG | GCAATGCCAA | CGCGGGCGCC | 240 |
| AACGACCCGA | GCAAGAACGA | CCCGAGCAAG | AGCCAGGCTC | CGCAGTCGGC | CAACAAGACC | 300 |
| GGCAACGTCG | ACGACGCCAA | CAACCAGGAT | CCGATGCAAG | CGCTGATGCA | GCTGCTGGAA | 360 |
| GACCTGGTGA | AGCTGCTGAA | GGCGGCCCTG | CACATGCAGC | AGCCCGGCGG | CAATGACAAG | 420 |
| GGCAACGGCG | TGGGCGGTGC | CAACGGCGCC | AAGGGTGCCG | GCGGCCAGGG | CGGCCTGGCC | 480 |
| GAAGCGCTGC | AGGAGATCGA | GCAGATCCTC | GCCCAGCTCG | GCGGCGGCGG | TGCTGGCGCC | 540 |
| GGCGGCGCGG | GTGGCGGTGT | CGGCGGTGCT | GGTGGCGCGG | ATGGCGGCTC | CGGTGCGGGT | 600 |
| GGCAAGGCG | GTGCGAACGG | CGCCGACGGC | GGCAATGGCG | TGAACGGCAA | CCAGGCGAAC | 660 |
| GGCCCGCAGA | ACGCAGGCGA | TGTCAACGGT | GCCAACGGCG | CGGATGACGG | CAGCGAAGAC | 720 |

-continued

| | | | | | | |
|---|---|---|---|---|---|---|
| CAGGGCGGCC | TCACCGGCGT | GCTGCAAAAG | CTGATGAAGA | TCCTGAACGC | GCTGGTGCAG | 780 |
| ATGATGCAGC | AAGGCGGCCT | CGGCGGCGGC | AACCAGGCGC | AGGGCGGCTC | GAAGGGTGCC | 840 |
| GGCAACGCCT | CGCCGGCTTC | CGGCGCGAAC | CCGGGCGCGA | ACCAGCCCGG | TTCGGCGGAT | 900 |
| GATCAATCGT | CCGGCCAGAA | CAATCTGCAA | TCCCAGATCA | TGGATGTGGT | GAAGGAGGTC | 960 |
| GTCCAGATCC | TGCAGCAGAT | GCTGGCGGCG | CAGAACGGCG | GCAGCCAGCA | GTCCACCTCG | 1020 |
| ACGCAGCCGA | TGTAA | | | | | 1035 |

Further information regarding the hypersensitive response elicitor polypeptide or protein derived from *Pseudomonas solanacearum* is set forth in Arlat, M., F. Van Gijsegem, J. C. Huet, J. C. Pemollet, and C. A. Boucher, "PopA1, a Protein which Induces a Hypersensitive-like Response in Specific Petunia Genotypes, is Secreted via the Hrp Pathway of *Pseudomonas solanacearum*," *EMBO J.* 13:543–533 (1994), which is hereby incorporated by reference.

The hypersensitive response elicitor polypeptide or protein from *Xanthomonas campestris* pv. glycines has an amino acid sequence corresponding to SEQ. ID. No. 9 as follows:

| | | | | | | | | | | | | | | | |
|---|---|---|---|---|---|---|---|---|---|---|---|---|---|---|---|
| Thr | Leu | Ile | Glu | Leu | Met | Ile | Val | Val | Ala | Ile | Ile | Ala | Ile | Leu | Ala |
| 1 | | | | 5 | | | | | 10 | | | | | 15 | |
| Ala | Ile | Ala | Leu | Pro | Ala | Tyr | Gln | Asp | Tyr | | | | | | |
| | | | 20 | | | | | 25 | | | | | | | |

This sequence is an amino terminal sequence having 26 residues only from the hypersensitive response elicitor polypeptide or protein of *Xanthomonas campestris* pv. glycines. It matches with fimbrial subunit proteins determined in other *Tanthomouas campestris* pathovars.

The above elicitors are exemplary. Other elicitors can be identified by growing bacteria that elicit a hypersensitive response under which genes encoding an elicitor are expressed. Cell-free preparations from culture supernatants can be tested for elicitor activity (i.e. local necrosis) by using them to infiltrate appropriate plant tissues.

It is also possible to use fragments of the above hypersensitive response elicitor polypeptides or proteins as well as fragments of full length elicitors from other pathogens, in the method of the present invention.

Suitable fragments can be produced by several means. In the first, subclones of the gene encoding a known elicitor protein are produced by conventional molecular genetic manipulation by subcloning gene fragments. The subclones then are expressed in vitro or in vivo in bacterial cells to yield a smaller protein or a peptide that can be tested for elicitor activity according to the procedure described below.

As an alternative, fragments of an elicitor protein can be produced by digestion of a full-length elicitor protein with proteolytic enzymes like chymotrypsin or Staphylococcus proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for increase and expression of a truncated peptide or protein.

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide.

The protein or polypeptide of the present invention is preferably produced in purified form (preferably at least about 80%, more preferably 90%, pure) by conventional techniques. Typically, the protein or polypeptide of the present invention is secreted into the growth medium of recombinant *E. coli*. To isolate the protein, the *E. coli* host cell carrying a recombinant plasmid is propagated, homogenized, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK ± or KS ± (see "Stratagene Cloning Systems" Catalog (1993) from Stratagene, La Jolla, Calif, which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, New York (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the PR and PL promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The method of the present invention can be utilized to treat a wide variety of plants to impart pathogen resistance. Suitable plants include dicots and monocots. More particularly, useful crop plants can include: rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane. Examples of suitable ornamental plants are: *Arabidopsis thaliana*, Saintpaulia, petunia, pelargonium, poinsettia, chrysanthemum, carnation, and zinnia.

The method of imparting pathogen resistance to plants in accordance with the present invention is useful in imparting resistance to a wide variety of pathogens including viruses, bacteria, and fungi.

Resistance, inter alia, to the following viruses can be achieved by the method of the present invention: *Tobacco mosaic* virus and tomato mosaic virus.

Resistance, inter alia, to the following bacteria can also be imparted to plants in accordance with the present invention: *Pseudomonas solancearum*, *Pseudomonas syringae* pv. *tabaci*, and *Xanthamonas campestris* pv. *pelargonii*.

Plants can be made resistant, inter alia, to the following fungi by use of the method of the present invention: *Fusarium oxysporum* and *Phytophthora infestans*.

The method of the present invention can be carried out through a variety of procedures for applying the hypersensitive response elicitor polypeptide or protein to all or part of the plant being treated. This may (but need not) involve infiltration of the hypersensitive response elicitor polypeptide or protein into the plant. Suitable application methods include high or low pressure spraying, injection, and leaf abrasion proximate to when elicitor application takes place. Other suitable application procedures can be envisioned by those skilled in the art provided they are able to effect contact of the hypersensitive response elicitor polypeptide or protein with cells of the plant.

The hypersensitive response elicitor polypeptide or protein can be applied to plants in accordance with the present invention alone or in a mixture with other materials.

One aspect of the present invention involves a composition for imparting pathogen resistance to plants containing a hypersensitive response elicitor polypeptide or protein in a carrier. Suitable carriers include water or aqueous solutions. In this embodiment, the composition contains greater than 500 nM hypersensitive response elicitor polypeptide or protein.

Although not required, this composition may contain additional additives including fertilizer, insecticide, fungicide, and mixtures thereof. Suitable fertilizers include $(NH_4)_2NO_3$. An example of a suitable insecticide is Malathion. Useful fungicides include Captan.

Other suitable additives include buffering agents, wetting agents, and abrading agents. These materials can be used to facilitate the process of the present invention.

EXAMPLES

Example 1

Harpin-induced Resistance of Tomato Against the Southern Bacterial Wilt Disease (*Pseudomonas solanacearum*)

Two-week-old tomato seedlings, grown in 8×15 cm flats in the greenhouse were treated as follows: 20 plants were used for each of the six treatments, which were designated A through F, and are described as follows:

(A) About 100 μl of a 200 μg/ml crude harpin (i.e. hypersensitive response elicitor polypeptide or protein) preparation (Z-M. Wei, "Harpin, Elicitor of the Hypersensitive Response Produced by the Plant Pathogen *Erwinia amylovora,*" *Science* 257:85–88 (1992), which is hereby incorporated by reference) was infiltrated into the lowest true leaf of each of the seedlings.

(B) The same harpin preparation as used in (A) was sprayed with 400-mesh carborundum onto the leaf surface of the seedlings and then gently rubbed in with the thumb.

(C) *E. coli* DH5(pCPP430)(See FIG. 1 for map of plasmid vector pCPP430) was grown in LB medium to $OD_{620}$= 0.7. The culture was centrifuged and then resuspended in 5 mM of potassium phosphate buffer pH 6.5. About 100 μl of cell suspension was infiltrated into each leaf of the seedlings.

(D) *E. coli* DH5(pCPP430::hrpN) (See FIG. 1 for map of plasmid vector pCPP430::hrpN) was used as in (C). The cells were grown, and the suspension and the amount of inoculum used were the same as described in (C).

Figure 2:
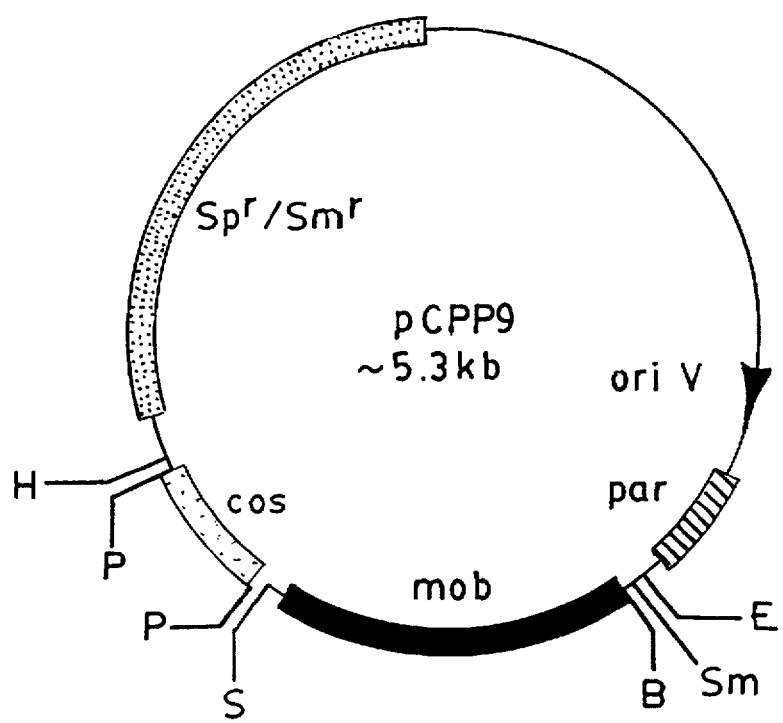

(E) For *E. coli* DH5(pCPP9) (See FIG. 2), the cells were grown and the suspension and the amount of inoculum used were the same as described in (C).

(F) Infiltration of leaves with 5mM potassium phosphate buffer was as described in (C).

The challenge pathogenic bacterium, *Pseudomonas solanacearum* strain K60, was grown in King's medium B to $OD_{620}$=0.7 (about $10^8$ cfu/ml). The culture was centrifuged and resuspended in 100 volume of 5 mM potassium phosphate buffer to a final concentration of about $1 \times 10^6$ cfu/ml.

Three days after the tomato seedlings were treated with harpin or bacteria, they were pulled up and about one cm of roots were cut off with scissors. The seedlings were then dipped into the suspension of *P. solanacearum* K60 for 3 min. The inoculated plants were replanted into the same pots. The plants were left in a greenhouse, and the disease incidence was recorded 7 days after inoculation.

A. Effect of treatment with harpin

After 24 hours, only those leaf portions that had been infiltrated with harpin or *E. coli* DH5(pCPP430) had collapsed. Leaves sprayed with harpin and carborundum showed only spotty necrosis.

B. Effect of treatment with harpin on the development of Southern Bacterial Wilt None of the 20 harpin-infiltrated plants showed any symptoms one week after inoculation with *P. solanacearum* K60 (Table 1). One out of the 20 plants showed stunting symptoms. However, 7 of the 20 buffer-infiltrated plants showed stunting symptoms. Treatment with *E. coli* DH5 (pCPP430⁻) (a transposon-induced mutant unable to elicit the hypersensitive collapse) or *E. coli* DH5(pCPP9) did not show significant difference compared to the plants treated with buffer. These results suggest that harpin or *E. coli* DH5(pCPP430), which produces harpin, induced resistance in the tomato plants to southern bacterial wilt caused by *P. solanacearum* K60.

TABLE 1

Disease incidence of tomato seedlings 7 and 14 days after inoculation with *P. solanacearum* K60.

| | Number of Plants | | | |
|---|---|---|---|---|
| | Day 7 | | Day 14 | |
| Treatment | Stunted | Healthy | Stunted | Healthy |
| A. Harpin infiltration | 0 | 20 | 2 | 18 |
| B. Harpin spray | 1 | 19 | 3 | 17 |
| C. *E. coli* DH5 (pCPP430) | 2 | 18 | 3 | 17 |
| D. *E. coli* DH5 (pCPP430⁻) | 4 | 16 | 7 | 13 |
| E. *E. coli* DH5 (pcPP9) | 5 | 15 | 6 + 1 wilted | 13 |
| F. Buffer | 7 | 13 | 8 + 1 wilted | 11 |
| No pathogen | 0 | 20 | 0 | 20 |

Four weeks after inoculation, plants treated with the harpin or *E. coli* DH5(pcPP430) were taller and broader as compared to those treated with buffer. The average heights of 10 plants that had been infiltrated with harpin or buffer are given in Table 2.

TABLE 2

Heights (cm) of tomato plants four weeks after inoculation with *Pseudomonas solanacearum* K60, following treatment with harpin or buffer.

| Infiltrated with Buffer Not inoculated | Infiltrated with Harpin Inoculated with K60 | Infiltrated with Buffer Inoculated with K60 |
|---|---|---|
| 36 | 32 | 11 |
| 41 | 29 | 21 |
| 35 | 38 | 33 |
| 34 | 35 | 12 |

TABLE 2-continued

Heights (cm) of tomato plants four weeks after inoculation with
*Pseudomonas solanacearum* K60, following treatment with harpin or buffer.

| Infiltrated with Buffer Not inoculated | | Infiltrated with Harpin Inoculated with K60 | Infiltrated with Buffer Inoculated with K60 |
|---|---|---|---|
| | 39 | 37 | 15 |
| | 35 | 33 | 32 |
| | 36 | 22 | 25 |
| | 35 | 35 | 15 |
| | 41 | 40 | 37 |
| | 37 | 29 | 38 |
| Average | 36.9 | 33 | 23.9 |

Example 2

Harpin-induced Resistance of Tomato against Southern Bacterial Wilt Disease Pseudomonas solanacearum All the methods used for infiltration and inoculation were the same as described in Example 1, except that the concentration of *P. solanacearum* K60 was about $5 \times 10^4$ cfu/ml.

The buffer-infiltrated plants showed symptoms 15 days after inoculation with *P. solanacearum* K60. Six out of 20 plants showed stunting symptoms after 15 days; 2 plants were wilted after 21 days. The wilted plants eventually died. However, none of the 20 harpin-treated plants showed stunting symptoms. Three weeks after inoculation, 3 of the 20 harpin-treated plants showed stunting symptoms. It is possible that after three weeks, the plants may have lost their induced resistance. As in the first experiment, the overall girth and heights of the harpin-treated plants were greater than those treated with buffer.

Example 3

Harpin-induced Resistance of Tomato against Southern Bacterial Wilt Disease *Pseudomonas solanacearum*

This experiment was similar to Example 1, except that additional inoculum of *Pseudomonas solanacearum* K60 was added to the pots containing the treated tomato plants.

Harpin was infiltrated into two-week-old tomato seedlings. Two panels of each plant were infiltrated with about 200 µl harpin suspended in 5 mM of potassium phosphate buffer at the concentration about 200 µg/ml. A total of 20 tomato seedlings were infiltrated. The same number of tomato seedlings were infiltrated with buffer. After two days, the plants were inoculated with *Pseudomonas solanacearum* K60 by root-dipping. The harpin- or buffer-infiltrated plants were pulled from the soil mix and small amounts of roots were cut off with scissors and then the remaining roots were dipped into a suspension of *P. solanacearum* K60 for three minutes. The concentration of the bacterial cell suspension was about $5 \times 10^8$ cfu/ml. The seedlings were replanted into the same pot. An additional 3 ml of bacterial suspension was added to the soil of each individual 4-inch diameter pot. Disease incidence was scored after one week. All the experiments were done in the greenhouse with limited temperature control.

After three weeks, 11 of the 20 buffer-infiltrated tomato plants had died and 2 plants that had wilted recovered, but remained severely stunted. Only 4 plants grew normally compared with non-inoculated tomatoes. However, 15 of the harpited plants appeared healthy; three plants were stunted and two plants were wilted 3 weeks after inoculation. These results are summarized below in Table 3.

TABLE 3

Harpin-induced resistance of tomato against bacterial wilt disease caused by *P. solanacearum*

| | Weeks After Inoculation | | |
|---|---|---|---|
| Treatment | 1 | 2 | 3 |
| Harpin | | | |
| Healthy | 20 | 17 | 15 |
| Wilted | 0 | 1 | 2 |
| Stunted | 0 | 2 | 3 |
| Buffer | | | |
| Healthy | 8 | 5 | 4 |
| Wilted | 8 | 12 | 13 |
| Stunted | 4 | 3 | 3 |

Example 4

Harpin-induced Resistance of Tobacco to Tobacco Mosaic Virus

One panel of a lower leaf of four-week old tobacco seedlings (cultivar, Xanthi, with N gene) were infiltrated with *E. amylovora* harpin at the concentration of 200 µg/ml. After three days, the plants were challenged with tobacco mosaic virus ("TMV"). Two concentrations of the virus (5 µg and 100 µg/ml) were used. About 50 µl of the virus suspension was deposited on one upper tobacco leaf. The leaf was dusted with 400-mesh carborundum and the leaves gently rubbed. Each concentration was tested on three plants. Necrotic lesions were counted 4 days after inoculation and on two subsequent days and the mean number on three leaves is reported (Table 4). It was difficult to distinguish the individual lesions by Day 10 because some of the necrotic lesions had merged together. Therefore, the number of lesions recorded seemed less than those recorded on Day 7. The size of the necrotic lesions in buffer-treated leaves was much larger than the harpin-treated leaves.

TABLE 4

Harpin-induced resistance of tobacco against TMV from inoculation with 5 µg/ml of virus

| | Mean Number of Lesions/Leaf | | |
|---|---|---|---|
| Treatment | Day 4 | Day 7 | Day 10 |
| Harpin | 21 | 32 | 35 |
| Buffer | 67 | 102 | 76 |

There was no significant difference in the number of local lesions that developed on the harpin-treated and buffer-treated tobacco when the tobacco mosaic virus inoculum concentration was 100 µg/ml.

Example 5

Harpin-induced Resistance of Tomato to Fusarium Wilt Disease

Six-week-old tomato plants were treated with harpin as described for Example 3. The fungal pathogen, *Fusarium oxysporum*, was grown on Lima Bean Agar medium for 5 days at 27° C. Two entire agar plates with mycelia were blended for 2 minutes in 20 ml of 5 mM potassium phosphate buffer. The roots of harpin- or buffer-treated tomato plants were wounded by plunging a wooden stake into the soil of the pots. Then, 3 ml of the fungal suspension was poured into the soil of each 4-inch pot. The inoculated plants remained in a controlled environment chamber at 24° C. with 16 hours of light per day. Disease incidence was recorded 7 days after inoculation. Each treatment was applied to 10 plants. The results are shown below in Table 5.

TABLE 5

Effect of harpin or buffer treatment on Fusarium wilt disease of tomato

| Treatment | Number of plants (of 10) showing wilt symptoms at the indicated time post-inoculation | | | |
|---|---|---|---|---|
| | Day 7 | Day 10 | Day 15 | Day 20 |
| Harpin | 1 | 2 | 4 | 4 (1 dead) |
| Buffer | 3 | 6 | 7 | 7 (4 dead) |

Example 6

Harpin-Induced Resistance of Tobacco Against Wildfire Disease (*Pseudomonas syringae* pv. *tabaci*).

Harpin was infiltrated into single panels of the lower leaves of 4-week-old tobacco plants (20 cm high). After three days, suspensions of *Pseudomonas syringe* pv. *tabaci* were infiltrated into single panels of upper leaves. Four days later, disease incidence was recorded, as set forth in Table 6.

TABLE 6

Symptoms of infection by Wildfire disease in tobacco leaves inoculated with *Pseudomonas* syringe pv. *tabaci* following treatment of lower leaves with harpin.

| Concentration of *P.s. tabaci* | Treated with Harpin | Not treated with Harpin |
|---|---|---|
| $10^4$ cfu/ml | no symptoms | necrosis and water-soaking |
| $10^5$ cfu/ml | no symptoms | necrosis and water-soaking |
| $10^6$ cfu/ml | no symptoms | necrosis and water-soaking |
| $10^7$ cfu/ml | no symptoms | necrosis and water-soaking |
| $10^8$ cfu/ml | necrosis | necrosis and water-soaking |

Example 7

Harpin-induced Resistance of Geranium (*Pelargonium hortorum*) Against Bacterial Leaf Spot (*Xanthamonas campestris* pv. *pelargonii*)

This experiment was done with rooted cuttings of geranium growing in individual 4" or 6" pots in an artificial soil mix in a greenhouse. Two lower leaves on each plant were infiltrated with either 0.05M potassium phosphate buffer, pH 6.5 (control), or harpin or a suspension of *Escherichia coli* DH5(pCPP430) (the entire cloned hrp gene cluster of *E. amylovora*). Two to seven days following infiltration, all the plants were inoculated with a pure culture of the bacterial leaf spot pathogen, *Xanthamonas campestris* pv. *pelargonii*. A suspension of the bacteria ($5 \times 10^6$ cfu/ml) was atomized over both upper and lower leaf surfaces of the plants at low pressure. Each treatment was applied to two plants (designated "A" and "B" in Table 7). The plants were maintained in a closed chamber for 48 hours with supplemental misting supplied by cool-mist foggers. Then, the plants were maintained on the greenhouse bench subject to ambient humidity and temperature of 23° C. to 32° C. for 10 days before disease development was assessed.

TABLE 7

Effect of harpin and the hrp gene cluster of *Erwinia amylovora* on the development of bacterial leaf spot of geranium.

| | Time between treatment and inoculation with *Xanthomonas campestris* pv. *pelargonii* | | | | | | | | |
|---|---|---|---|---|---|---|---|---|---|
| | 7 Days Plant | | 5 Days Plant | | 4 Days Plant | | 3 Days Plant | | 2 days Plant |
| Treatment | A | B | A | B | A | B | A | B | A | B |
| Buffer | 3* | 5 | 5 | 4 | 3 | 2 | 4 | 3 | 4 | 5 |
| Harpin | 0 | 0 | 0 | 0 | 0 | 0 | 1 | 0 | 0 | 0 |
| DH5 (pCPP430) | 0 | 0 | NT | NT | 0 | 0 | 0 | 1 | 1 | 0 |

*Numbers in table are the number of leaves showing disease symptoms (pronounced necrosis, chlorosis, or wilting) 10 days following inoculation.

Example 8

Activity of several harpins in inducing resistance to Wildfire Disease caused by *Pseudomonas syringae* pv. *tabaci*

Tobacco plants (*Nicotiana tabacum* var. Xanthi) were grown in the greenhouse. At 4 weeks of age, harpin preparations were infiltrated into a single panel of two lower leaves of each plant. Twelve plants were treated with each harpin preparation, and three were treated with the same potassium phosphate buffer that was used to prepare the harpins. The hypersensitive necrosis developed within 24 hours in the panels of the leaves infiltrated with the harpin preparations, but not with buffer.

At 7, 10, 11, and 12 days after harpin treatment, all plants were inoculated with suspensions of $10^4$ to $10^6$ cells/ml of *Pseudomonas syringae* pv. *tabaci* by infiltrating panels on upper leaves. Plants were incubated in the greenhouse for 7 days before disease development was evaluated. The results are tabulated as follows in Table 8:

TABLE 8

| Harpin source | Days between treatment and inoculation | | | | | | | | | | | |
|---|---|---|---|---|---|---|---|---|---|---|---|---|
| | 12 | | | 11 | | | 10 | | | 7 | | |
| log [Inoc.] | 4 | 5 | 6 | 4 | 5 | 6 | 4 | 5 | 6 | 4 | 5 | 6 |
| None (buffer) | + | + | ++ | + | + | ++ | + | + | ++ | + | + | ++ |
| *P. syringae* | − | − | + | − | − | + | − | − | + | − | − | + |
| *E. chrysanthemi* | − | − | + | − | − | + | − | − | + | − | − | + |
| *E. amylovora* | − | − | + | − | − | − | − | − | + | − | − | + |

− = No symptoms,
+ = Necrosis with yellow halo, typical of wildfire disease
++ = Severe necrosis with yellow halo, typical of wildfire disease The results indicate that the harpin preparations from the three bacteria are effective in inducing resistance to the wildfire pathogen. Plants treated with either harpin exhibited no symptoms with the two lower inoculum concentrations used. At the higher concentration, symptoms were more severe on buffer-treated plants than harpin-treated plants.

Example 9

Harpin induced resistance against the Late Blight disease caused by *Phytophthora infestans*

The late blight pathogen affects potatoes and tomatoes primarily. It was responsible for the infamous Irish potato famine. The activity of harpin in inducing resistance to this pathogen was tested on tomato seedlings grown in the greenhouse. Three-week old seedlings (cultivar 'Mama Mia', about 6 to 8 inches high) were treated with harpin and subsequently inoculated with *Phythophthora infestans*. Two panels of a lower leaf of each plant were infiltrated with a solution of harpin, a suspension of *Escherichia coli* DH5 (pCPP430), which produces and secretes harpin, or potassium phosphate buffer.

Two, three, or four days following infiltration, the plants were inoculated with a mycelial suspension of *Phytophthora infestans*. The strain U.S. 7 was used, which is highly virulent to tomato. The mycelial suspension was made by blending gently the contents of two barley-meal agar plates on and in which the fungus had grown for 2 weeks at 21° C. The suspension was brushed onto the top and undersides of one leaf per treated plant with an artist's broad paint brush.

The treated and inoculated plants were incubated in a specially constructed mist chamber designed to maintain a temperature of 20°-23° C. in the greenhouse, while maintaining high relative humidity. The moisture was provided by several cool-mist foggers operating at maximum rate on purified water. Disease incidence was evaluated 13 days following inoculation with *Phytophthora infestans*, and the results are tabulated in Table 9. Each treatment was applied to four individual plants.

TABLE 9

Numbers of lesion of late blight that were present on tomato leaves 13 days after inoculation.

| | Days between treatment and inoculation | | | | | | | | | | |
|---|---|---|---|---|---|---|---|---|---|---|---|
| | 4 | | | | 3 | | | | 2 | | |
| | Plant | | | | | | | | | | |
| Treatment | A | B | C | D | A | B | C | D | A | B | C | D |
| Buffer | 3 | 2 | 0 | 0 | 1 | 2 | 2 | 0 | 0 | 0 | 4 | 1 |
| Harpin | 0 | 0 | 1 | 0 | 0 | 0 | 0 | 1 | 2 | 1 | 0 | 0 |
| DH5(pCPP430) | 0 | 0 | 0 | 1 | 0 | 2 | 2 | 1 | 0 | 1 | 1 | 0 |

Treatment with harpin reduced the number of lesions that developed on plants at all intervals between treatment and inoculation. The number of late blight lesions that developed also was reduced by prior treatment with DH5(pCPP430), which produces and secretes harpin.

Although the invention has been described in detail for the purpose of illustration, it is understood that such detail is solely for that purpose, and variations can be made therein by those skilled in the art without departing from the spirit and scope of the invention which is defined by the following claims.

---

What is claimed:

1. A method of imparting pathogen resistance to plants comprising:
applying externally to a plant a hypersensitive response eliciting bacterium, which does not cause disease in that plant, or a hypersensitive response eliciting polypeptide or protein, wherein the hypersensitive response eliciting polypeptide or protein corresponds to that derived from a pathogen selected from the group consisting of Erwinia amylovora, Erwinia chrysanthemi, Pseudomonas syringae, Pseudomonas solancearum, Xanthamonas campestris, and mixtures thereof.

2. A method according to claim 1, wherein the hypersensitive response eliciting polypeptide or protein corresponds to that derived from Erwinia chrysanthemi.

3. A method according to claim 2, wherein the hypersensitive response eliciting polypeptide or protein has an amino acid sequence corresponding to SEQ. ID. No. 1.

4. A method according to claim 2, wherein the hypersensitive response eliciting polypeptide or protein has a molecular weight of 34 kDa.

5. A method according to claim 1, wherein the hypersensitive response eliciting polypeptide or protein corresponds to that derived from Erwinia amylovora.

6. A method according to claim 5, wherein the hypersensitive response eliciting polypeptide or protein has an amino acid sequence corresponding to SEQ. ID. No. 3.

7. A method according to claim 5, wherein the hypersensitive response eliciting polypeptide or protein has a molecular weight of 37 kDa.

8. A method according to claim 1, wherein the hypersensitive response eliciting polypeptide or protein corresponds to that derived from *Pseudomonas syringae*.

9. A method according to claim 8, wherein the hypersensitive response eliciting polypeptide or protein has an amino acid sequence corresponding to SEQ. ID. No. 5.

10. A method according to claim 8, wherein the hypersensitive response eliciting polypeptide or protein has a molecular weight of 34–35 kDa.

11. A method according to claim 1, wherein the hypersensitive response eliciting polypeptide or protein corresponds to that derived from *Pseudomonas solanacearum*.

12. A method according to claim 11, wherein the hypersensitive response eliciting polypeptide or protein has an amino acid sequence corresponding to SEQ. ID. No. 7.

13. A method according to claim 1, wherein the hypersensitive response eliciting polypeptide or protein corresponds to that derived from *Xanthomonas campestris*.

14. A method according to claim 13, wherein the hypersensitive response eliciting polypeptide or protein has an amino acid sequence corresponding to SEQ. ID. No. 9.

15. A method according to claim 1, wherein the plant is selected from the group consisting of dicots and monocots.

16. A method according to claim 15, wherein the plant is selected from the group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, and sugarcane.

17. A method according to claim 15, wherein the plant is selected from the group consisting of *Arabidopsis thaliana*, Saintpaulia, petunia, pelargonium, poinsettia, chrysanthemum, carnation, and zinnia.

18. A method according to claim 1, wherein the pathogen to which the plant is resistant is selected from the group consisting of a viruses, bacteria, fungi, and combinations thereof.

19. A method according to claim 1, wherein said applying is carried out by spraying.

20. A method according to claim 1, wherein the hypersensitive response eliciting polypeptide or protein is applied to plants as a composition further comprising a carrier.

21. A method according to claim 20, wherein the carrier is selected from the group consisting of water and aqueous solutions.

22. A method according to claim 20, wherein the composition contains greater than 500 nM of the hypersensitive response eliciting polypeptide or protein.

23. A method according to claim 20, wherein the composition further contains additives selected from the group consisting of fertilizer, insecticide, fungicide, and mixtures thereof.

24. A method according to claim 1, wherein the hypersensitive response eliciting polypeptide or protein is in isolated form.

25. A method according to claim 1, wherein the hypersensitive response eliciting polypeptide or protein is applied as bacteria which do not cause disease and are transformed with a gene encoding the hypersensitive response eliciting polypeptide or protein.

26. A method according to claim 1, wherein the hypersensitive response eliciting polypeptide or protein is applied as bacteria which cause disease in some plant species, but not in those subjected to said applying, and contain a gene encoding the hypersensitive response eliciting polypeptide or protein.

* * * * *